(12) United States Patent
An et al.

(10) Patent No.: US 10,906,914 B2
(45) Date of Patent: Feb. 2, 2021

(54) FUROQUINOLINEDIONES AS INHIBITORS OF TDP2

(71) Applicants: Linkun An, Guangzhou (CN); THE UNITED STATES OF AMERICA, AS REPRESENTED BY THE SECRETARY, DEPARTMENT OF HEALTH AND HUMAN SERVICES, Bethesda, MD (US)

(72) Inventors: Linkun An, Guangzhou (CN); Christophe Marchand, Silver Spring, MD (US); Yves Pommier, Bethesda, MD (US)

(73) Assignees: THE UNITED STATES OF AMERICA, AS REPRESENTED BY THE SECRETARY, DEPARTMENT OF HEALTH AND HUMAN SERVICES, Bethesda, MD (US); SUN YAT-SEN UNIVERSITY, Guangzhou (CN)

( * ) Notice: Subject to any disclaimer, the term of this patent is extended or adjusted under 35 U.S.C. 154(b) by 0 days.

(21) Appl. No.: 15/542,560

(22) PCT Filed: Jan. 8, 2016

(86) PCT No.: PCT/US2016/012672
§ 371 (c)(1),
(2) Date: Jul. 10, 2017

(87) PCT Pub. No.: WO2016/112304
PCT Pub. Date: Jul. 14, 2016

(65) Prior Publication Data
US 2018/0009822 A1    Jan. 11, 2018

Related U.S. Application Data

(60) Provisional application No. 62/100,968, filed on Jan. 8, 2015.

(51) Int. Cl.
| | | |
|---|---|---|
| C07D 491/048 | (2006.01) |
| C07D 471/04 | (2006.01) |
| A61K 31/122 | (2006.01) |
| C07D 498/04 | (2006.01) |
| C07D 491/04 | (2006.01) |
| A61K 31/498 | (2006.01) |
| A61K 31/475 | (2006.01) |
| A61K 31/47 | (2006.01) |
| A61K 31/136 | (2006.01) |
| A61K 31/7048 | (2006.01) |
| A61K 31/194 | (2006.01) |
| A61K 31/704 | (2006.01) |
| A61K 31/343 | (2006.01) |
| A61K 31/473 | (2006.01) |
| A61K 31/4741 | (2006.01) |
| A61K 31/4745 | (2006.01) |
| A61K 31/496 | (2006.01) |
| A61K 31/5377 | (2006.01) |
| A61K 45/06 | (2006.01) |
| C07D 221/08 | (2006.01) |
| C07D 307/92 | (2006.01) |

(52) U.S. Cl.
CPC ........ *C07D 491/048* (2013.01); *A61K 31/122* (2013.01); *A61K 31/136* (2013.01); *A61K 31/194* (2013.01); *A61K 31/343* (2013.01); *A61K 31/47* (2013.01); *A61K 31/473* (2013.01); *A61K 31/475* (2013.01); *A61K 31/4741* (2013.01); *A61K 31/4745* (2013.01); *A61K 31/496* (2013.01); *A61K 31/498* (2013.01); *A61K 31/5377* (2013.01); *A61K 31/704* (2013.01); *A61K 31/7048* (2013.01); *A61K 45/06* (2013.01); *C07D 221/08* (2013.01); *C07D 307/92* (2013.01); *C07D 471/04* (2013.01); *C07D 491/04* (2013.01); *C07D 498/04* (2013.01)

(58) Field of Classification Search
CPC .............. C07D 491/048; C07D 221/08; C07D 307/92; A61K 31/122
USPC .......................................................... 546/89
See application file for complete search history.

(56) References Cited

U.S. PATENT DOCUMENTS 6,395,773 B1    5/2002  Hirai et al.
2017/0015677 A1*  1/2017  Ban ...................... A61K 31/381

FOREIGN PATENT DOCUMENTS

CA      2107806 A1    4/1994
JP      63196576 A    8/1988
(Continued)

OTHER PUBLICATIONS

A fluopol—ABPP HTSassay to identify PAD inhibitors Bryan Knuckley et al (Year: 2010).*
(Continued)

*Primary Examiner* — Rita J Desai
(74) *Attorney, Agent, or Firm* — Cantor Colburn LLP

(57) ABSTRACT

Compounds of Formula I and the pharmaceutically acceptable salts thereof are disclosed Formula I. The variables $X^1$, $X^2$, and $R^{1-4}$ are disclosed herein. The compounds are useful for treating cancer and related proliferative diseases. Pharmaceutical compositions containing compounds of Formula I and methods of treatment comprising administering compounds of Formula I are also disclosed.

(Continued)

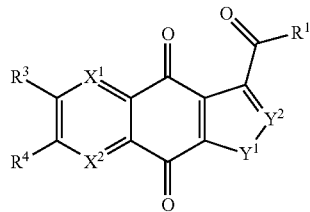

(I)

17 Claims, No Drawings

(56) References Cited

FOREIGN PATENT DOCUMENTS

| JP | H0990652 A | 4/1997 |
|---|---|---|
| WO | 2004087153 A2 | 10/2004 |
| WO | 2008052352 A1 | 5/2008 |
| WO | 2009036059 A2 | 3/2009 |
| WO | 2012024818 A1 | 3/2012 |
| WO | 2012119265 A1 | 9/2012 |
| WO | 2013166618 A1 | 11/2013 |

OTHER PUBLICATIONS

Amal S Yanni et al , Synthesis and application of some new Furoquinolinediones as Bactercides. (Year: 1990).*

Myung-Eun Suh et al . The 3-D QSAR study of anticancer 1-N-substitued Imidazo-and Pyrrolo-quinoline-4,9-dione Derivatives . . . (Year: 2001).*
Myung Eun Suh et al . Cytotoxic Effects of Pyridino[2,3-f]indole-4,9-diones on human tumor cell lines (Year: 2000).*
Griesbeck product Subclass2; Oxygen abd Sulfur containing heterene Quinones (Year: 2006).*
Cherkaoui, Omar, et al., "Regiospecific Hetero Diels-Alder Synthesis of Furo[2,3-g] and Furo[3,2-g]quinoline-4,9-diones," Tetrahedron; 1996, vol. 52, No. 28, pp. 9499-9508.
International Preliminary Report on Patentability; International Application No. PCT/US2016/012672; International Filing Date: Jan. 8, 2016; dated Jul. 20, 2017; 7 pages.
International Search Report; International Application No. PCT/US2016/012672; International Filing Date: Jan. 8, 2016; dated Mar. 21, 2016; 3 pages.
Nebois, P., et al., "In vitro cytotoxic activity of naphtol[1,2-b]furan, furo[2,3f], furo[2,3-g] and furo[3,2-g]quinoline derivatives," Pharmazie; Mar. 1999, vol. 54, Issue 3, pp. 215-218.
Nebois, P., et al., "Quinonic Derivatives Active Against a Virulent Strain of Toxoplasma gondii. Synthesis of 2-Methylfuro[2,3-g]- and [3,2-g]isoquinolinetriones," Bioorganic & Medicinal Chemistry Letters; 2000, vol. 10, pp. 871-873.
Raoof, A., et al., "Toxoflavins and Deazaflavins as the First Reported Selective Small Molecule Inhibitors of Tyrosyl-DNA Phosphodiesterase II," Journal of Medicinal Chemistry; 2013, vol. 56, pp. 6352-6370.
Written Opinion of the International Searching Authority; International Application No. PCT/US2016/012672; International Filing Date: Jan. 8, 2016; dated Mar. 21, 2016; 6 pages.
Yanni, Amal S., et al., "Synthesis and Application of some New Quinolinofurandione Derivatives as Bactericides," Indian Chem. Soc.; Sep. 1990, pp. 777-779, vol. 67.
Yanni et al. "Synthesis and Application of Some New Furoquinolinediones as Bactericides," Collection of Czechoslovak Chemical Communications, Institute of Organic Chemistry & Biochemistry, (1991), vol. 56, No. 3, pp. 706-711.

* cited by examiner

FUROQUINOLINEDIONES AS INHIBITORS OF TDP2

CROSS REFERENCE TO RELATED APPLICATION

This application is a U.S. National Stage Application of PCT/US2016/012672 filed Jan. 8, 2016, which claims priority from U.S. Provisional Application No. 62/100,968, filed Jan. 8, 2015, both of which are hereby incorporated by reference in its entirety.

STATEMENT OF GOVERNMENT SUPPORT

This invention was made in part with government support from the National Institutes of Health. The government has certain rights in this invention.

BACKGROUND

Topoisomerases are a family of enzymes essential for relaxation of supercoiled DNA, required for transcription, replication, and chromosome segregation. Topoisomerases cleave the supercoiled nucleic acids, which relieves torsional strain, and then religate the cut strands. The essential role of toposiomerases in DNA replication has made these enzymes major targets for cancer therapy. Topoisomerase inhibitors, such as camptothecin and topotecan for topoisomerase 1 (Top1), and etoposide and doxorubicin for topoisomerase 2 (Top2), trap topoisomerase-DNA cleavage complexes, thereby preventing replication and triggering destruction by apoptosis.

Tyrosyl-DNA phosphodiesterases (TDPs) play an important role in the repair of trapped topoisomerase-DNA cleavage complexes. TDPs exist in two forms: TDP1, for resolving trapped Top1-DNA cleavage complexes, and TDP2, for resolving Top2-DNA cleavage complexes.

Because TDPs can repair a broad spectrum of nucleic acid lesions, inhibition of TDPs is an attractive target for therapeutic treatment of cancers, possibly as sole therapeutic agents. It has also been noted that TDP2 deficiency potentiates the antiproliferative activity of Top2 inhibitors in cells with defective cell checkpoints, thus TDP2 inhibitors may provide synergistic effects as a combination therapy with inhibitors of Top2, such as etoposide and doxorubicin. Similar synergistic effects would be expected with inhibitors of Top1 and TDP1. Therefore, identifying effective inhibitors of TDP1 and/or TDP2 would be important in providing new methods of treating cancer.

SUMMARY

Described herein are inhibitors of TDP2, their methods of manufacture, compositions containing the described compounds, and methods of use of the described compounds. In a first aspect, a compound of Formula I and the pharmaceutically acceptable salts of a compound of Formula I are provided Formula I within Formula I the following conditions are met.

$X^1$ is N or $CR^5$.

$X^2$ is N or $CR^6$.

At least one of $X^1$ or $X^2$ is N.

$R^1$ is hydroxyl, $C_1$-$C_6$alkyl, $C_1$-$C_6$alkoxy, $C_2$-$C_6$alkenyloxy, $C_2$-$C_6$alkynyloxy, or $C_3$-$C_7$cycloalkyloxy, where one or more methylene units in the alkyl, alkenyl, or alkynyl portion of $R^1$ is optionally and independently replaced with —O—, —S—, or —N($R^7$)—, and $R^1$ other than hydroxyl is substituted by 0-3 substituents independently chosen at each occurrence from halogen, hydroxyl, cyano, =N, =NOR$^7$, —CO$_2$H, —(CO)—O—$C_1$-$C_6$alkyl, —C(O)NR$^7$R$^8$, and —W—P(O)YR$^9$ZR$^{10}$.

Or $R^1$ can be —O-A-B, wherein O is an oxygen atom.

A is a linker consisting of a bond, an alkylene chain of 1 to 6 carbons, or a phenylene group.

B is a phenyl, or a 5 or 6 membered heterocycle having 1, 2, or 3 ring atoms independently chosen from N, O, and S, wherein B is substituted with 0-3 substituents independently chosen from halogen, hydroxyl, cyano, amino, —SH, $C_1$-$C_6$alkyl, $C_2$-$C_6$alkenyl, $C_2$-$C_6$alkynyl, $C_1$-$C_6$alkoxy, $C_2$-$C_6$alkanoyl, $C_1$-$C_6$thioalkyl, $C_1$-$C_6$haloalkyl, $C_1$-$C_6$haloalkoxy, —($C_0$-$C_6$alkyl)cycloalkyl, —($C_0$-$C_6$alkyl)CO$_2$H, —($C_0$-$C_6$alkyl)-(CO)—O—$C_1$-$C_6$alkyl, —($C_0$-$C_6$alkyl)C(O)NR$^7$R$^8$, —($C_0$-$C_6$alkyl)NR$^7$C(O)R$^8$, —($C_1$-$C_6$alkyl)alkoxy, —($C_1$-$C_6$alkyl)OH, —($C_0$-$C_6$alkyl)NR$^7$R$^8$, —SO$_2$—$C_1$-$C_6$alkyl, and —($C_0$-$C_6$alkyl)-W—P(O)YR$^9$ZR$^{10}$.

$Y^1$ is O, NH, or S.

$Y^2$ is N or $CR^2$.

$R^2$ is hydrogen, halogen, $C_1$-$C_6$alkyl, $C_1$-$C_6$alkoxy, $C_1$-$C_6$haloalkyl, $C_1$-$C_6$haloalkoxy, —($C_0$-$C_6$alkyl)cycloalkyl, —($C_0$-$C_6$alkyl)NR$^7$R$^8$, or phenyl, each $R^2$ other than hydrogen and hydroxyl being substituted with 0 to 3 groups chosen independently at each occurrence from halogen, hydroxyl, $C_1$-$C_6$alkyl, $C_1$-$C_6$alkoxy, $C_1$-$C_6$haloalkyl, and $C_1$-$C_6$haloalkoxy.

Or, $R^2$ is a group -J-Q, where J is a 1 to 4 carbon alkylene linker in which any —CH$_2$— group is optionally replaced by —C(O)O—, —C(O)NH—, —C(O)NR$^{11}$, or —C(O)—.

Q is $C_1$-$C_6$alkyl, $C_1$-$C_6$alkylamino, aryl, or heteroaryl, each of which is unsubstituted or substituted with one or more groups independently chosen from halogen, hydroxyl, amino, cyano, $C_1$-$C_4$alkyl, $C_1$-$C_4$alkoxy, $C_1$-$C_2$haloalkyl, and $C_1$-$C_2$haloalkoxy.

W, Y, and Z are independently at each occurrence a bond or O.

$R^3$, $R^4$, $R^5$, and $R^6$, are chosen independently at each occurrence from hydrogen, halogen, cyano, amino, $C_1$-$C_6$alkyl, —($C_0$-$C_6$alkyl)cycloalkyl, $C_1$-$C_6$alkoxy, $C_1$-$C_6$haloalkyl, and $C_1$-$C_6$haloalkoxy.

$R^7$, $R^8$, $R^9$ and $R^{19}$ are chosen independently at each occurrence from hydrogen, $C_1$-$C_6$alkyl, $C_2$-$C_6$alkenyl, —($C_0$-$C_6$alkyl)cycloalkyl, and $C_1$-$C_6$haloalkyl, and any $R^7$ and $R^8$ bound to the same nitrogen atom may be taken together to form a 4- to 7-membered heterocyloalkyl group substituted with 0 to 2 substituents chosen from hydroxyl, halogen, $C_1$-$C_4$alkyl, $C_1$-$C_4$alkoxy, and $C_2$-$C_4$alkanoyl.

$R^{11}$ is $C_1$-$C_6$alkyl or $C_1$-$C_6$alkylamino.

Wherein the compound is not:

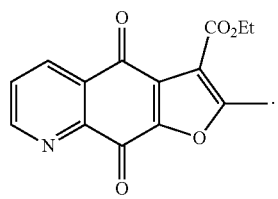 [SMILES: CCOC(=O)c1c(C)oc2c1C(=O)c1cccnc1C2=O]

Pharmaceutical compositions comprising a compound or salt of Formula I together with a pharmaceutically acceptable carrier are also disclosed.

Methods of treating a cancer responsive to TDP2 inhibition, comprising the step of administering to the patient in need thereof a compound or salt thereof, are also disclosed.

Methods of treating cancers, including glioma (glioblastoma), acute myelogenous leukemia, acute myeloid leukemia, myelodysplastic/myeloproliferative neoplasms, sarcoma, chronic myelomonocytic leukemia, non-Hodgkin's lymphoma, astrocytoma, melanoma, non-small cell lung cancer, small cell lung cancer, cervical cancer, rectal cancer, ovarian cancer, cholangiocarcinomas, chondrosarcoma, or colon cancer, comprising administering a therapeutically effective amount of a compound or salt of Formula I to a patient in need of such treatment are also disclosed.

DETAILED DESCRIPTION

Terminology

Compounds are described using standard nomenclature. Unless defined otherwise, all technical and scientific terms used herein have the same meaning as is commonly understood by one of skill in the art to which this invention belongs.

The terms "a" and "an" do not denote a limitation of quantity, but rather denote the presence of at least one of the referenced items. The term "or" means "and/or". The terms "comprising," "having," "including," and "containing" are to be construed as open-ended terms (i.e., meaning "including, but not limited to").

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art of this disclosure.

Furthermore, the disclosure encompasses all variations, combinations, and permutations in which one or more limitations, elements, clauses, and descriptive terms from one or more of the listed claims are introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group.

All compounds are understood to include all possible isotopes of atoms occurring in the compounds. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$.

Formula I includes all pharmaceutically acceptable salts of Formula I.

The opened ended term "comprising" includes the intermediate and closed terms "consisting essentially of" and "consisting of."

The term "substituted" means that any one or more hydrogens on the designated atom or group is replaced with a selection from the indicated group, provided that the designated atom's normal valence is not exceeded. When the substituent is oxo (i.e., =O), then 2 hydrogens on the atom are replaced. When aromatic moieties are substituted by an oxo group, the aromatic ring is replaced by the corresponding partially unsaturated ring. For example a pyridyl group substituted by oxo is a pyridone. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent.

Suitable groups that may be present on an "optionally substituted" position include, but are not limited to, e.g., halogen, cyano, hydroxyl, amino, nitro, oxo, azido, alkanoyl (such as a $C_2$-$C_6$ alkanoyl group such as acyl or the like (—(CO)alkyl)); carboxamido; alkylcarboxamide; alkyl groups, alkoxy groups, alkylthio groups including those having one or more thioether linkages, alkylsulfinyl groups including those having one or more sulfinyl linkages, alkylsulfonyl groups including those having one or more sulfonyl linkages, mono- and di-aminoalkyl groups including groups having one or more N atoms, all of the foregoing optional alkyl substituents may have one or more methylene groups replaced by an oxygen or —NH—, and have from about 1 to about 8, from about 1 to about 6, or from 1 to about 4 carbon atoms, cycloalkyl; phenyl; phenylalkyl with benzyl being an exemplary phenylalkyl group, phenylalkoxy with benzyloxy being an exemplary phenylalkoxy group. Alkylthio and alkoxy groups are attached to the position they substitute by the sulfur or oxygen atom respectively.

A dash ("-") that is not between two letters or symbols is used to indicate a point of attachment for a substituent.

"Alkyl" includes both branched and straight chain saturated aliphatic hydrocarbon groups, having the specified number of carbon atoms, generally from 1 to about 8 carbon atoms. The term $C_1$-$C_6$alkyl as used herein indicates an alkyl group having from 1, 2, 3, 4, 5, or 6 carbon atoms. Other embodiments include alkyl groups having from 1 to 8 carbon atoms, 1 to 4 carbon atoms or 1 or 2 carbon atoms, e.g. $C_1$-$C_8$alkyl, $C_1$-$C_4$alkyl, and $C_1$-$C_2$alkyl. When $C_0$-$C_n$ alkyl is used herein in conjunction with another group, for example, —$C_0$-$C_2$alkyl(phenyl), the indicated group, in this case phenyl, is either directly bound by a single covalent bond ($C_0$alkyl), or attached by an alkyl chain having the specified number of carbon atoms, in this case 1, 2, 3, or 4 carbon atoms. Alkyls can also be attached via other groups such as heteroatoms as in —O—$C_0$-$C_4$alkyl($C_3$-$C_7$cycloalkyl). Examples of alkyl include, but are not limited to, methyl, ethyl, n-propyl, isopropyl, n-butyl, 3-methylbutyl, t-butyl, n-pentyl, and sec-pentyl.

"Alkenyl" is a branched or straight chain aliphatic hydrocarbon group having one or more carbon-carbon double bonds that may occur at any stable point along the chain, having the specified number of carbon atoms. Examples of alkenyl include, but are not limited to, ethenyl and propenyl.

"Alkynyl" is a branched or straight chain aliphatic hydrocarbon group having one or more double carbon-carbon triple bonds that may occur at any stable point along the chain, having the specified number of carbon atoms.

"Alkoxy" is an alkyl group as defined above with the indicated number of carbon atoms covalently bound to the group it substitutes by an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. Similarly an "Alkylthio" or a "thioalkyl" group is an alkyl group as defined above with the indicated number of carbon atoms covalently bound to the group it substitutes by a sulfur bridge (—S—). Similarly, "alkenyloxy", "alkynyloxy", and "cycloalkyloxy" refer to alkenyl, alkynyl, and cycloalkyl groups, in each instance covalently bound to the group it substitutes by an oxygen bridge (—O—).

"Alkanoyl" is an alkyl group as defined above with the indicated number of carbon atoms covalently bound to the group it substitutes via keto (—C(O)—) group. The carbon of the keto group is included in the number of carbon atoms in the alkanoyl group, i.e. $C_2$ alkanoyl is —C(O))$CH_3$.

"Alkylene" is a chain of one or more methylene groups with attachment points on each end such that it can link two other groups, i.e. the alkylene group is —$(CH_2)_n$—.

"Cycloalkyl" is a saturated hydrocarbon ring group, having the specified number of carbon atoms, usually from 3 to about 7 carbon atoms. Examples of cycloalkyl groups include cyclopropyl, cyclobutyl, cyclopentyl, or cyclohexyl as well as bridged or caged saturated ring groups such as norborane or adamantane. "—($C_0$-$C_n$alkyl)cycloalkyl" is a cycloalkyl group attached to the position it substitutes either by a single covalent bond ($C_0$) or by an alkylene linker having 1 to n carbon atoms.

"Halo" or "halogen" means fluoro, chloro, bromo, or iodo.

"Heteroaryl" is a stable monocyclic aromatic ring having the indicated number of ring atoms which contains from 1 to 3, or in some embodiments from 1 to 2, heteroatoms chosen from N, O, and S, with remaining ring atoms being carbon, or a stable bicyclic or tricyclic system containing at least one 5- to 7-membered aromatic ring which contains from 1 to 3, or in some embodiments from 1 to 2, heteroatoms chosen from N, O, and S, with remaining ring atoms being carbon. Monocyclic heteroaryl groups typically have from 5 to 7 ring atoms. In some embodiments bicyclic heteroaryl groups are 9- to 10-membered heteroaryl groups, that is, groups containing 9 or 10 ring atoms in which one 5- to 7-member aromatic ring is fused to a second aromatic or non-aromatic ring. When the total number of S and O atoms in the heteroaryl group exceeds 1, these heteroatoms are not adjacent to one another. It is preferred that the total number of S and O atoms in the heteroaryl group is not more than 2. It is particularly preferred that the total number of S and O atoms in the aromatic heterocycle is not more than 1. Heteroaryl groups include, but are not limited to, oxazolyl, piperazinyl, pyranyl, pyrazinyl, pyrazolopyrimidinyl, pyrazolyl, pyridizinyl, pyridyl, pyrimidinyl, pyrrolyl, quinolinyl, tetrazolyl, thiazolyl, thienylpyrazolyl, thiophenyl, triazolyl, benzo[d]oxazolyl, benzofuranyl, benzothiazolyl, benzothiophenyl, benzoxadiazolyl, dihydrobenzodioxynyl, furanyl, imidazolyl, indolyl, and isoxazolyl.

"Heterocycle" is a saturated, unsaturated, or aromatic cyclic group having the indicated number of ring atoms containing from 1 to about 3 heteroatoms chosen from N, O, and S, with remaining ring atoms being carbon. Examples of heterocycle groups include piperazine and thiazole groups.

"Heterocycloalkyl" is a saturated cyclic group having the indicated number of ring atoms containing from 1 to about 3 heteroatoms chosen from N, O, and S, with remaining ring atoms being carbon. Examples of heterocycloalkyl groups include tetrahydrofuranyl and pyrrolidinyl groups.

"Haloalkyl" means both branched and straight-chain alkyl groups having the specified number of carbon atoms, substituted with 1 or more halogen atoms, generally up to the maximum allowable number of halogen atoms. Examples of haloalkyl include, but are not limited to, trifluoromethyl, difluoromethyl, 2-fluoroethyl, and penta-fluoroethyl.

"Haloalkoxy" is a haloalkyl group as defined above attached through an oxygen bridge (oxygen of an alcohol radical).

"Phenylene" is a benzene ring with two different attachment points such that it can link two other groups, i.e. the phenylene group is —$(C_6H_4)$—. The attachment points can be ortho., mew, or para to each other.

"Pharmaceutical compositions" means compositions comprising at least one active agent, such as a compound or salt of Formula I, and at least one other substance, such as a carrier. Pharmaceutical compositions meet the U.S. FDA's GMP (good manufacturing practice) standards for human or non-human drugs.

"Carrier" means a diluent, excipient, or vehicle with which an active compound is administered. A "pharmaceutically acceptable carrier" means a substance, e.g., excipient, diluent, or vehicle, that is useful in preparing a pharmaceutical composition that is generally safe, non-toxic and neither biologically nor otherwise undesirable, and includes a carrier that is acceptable for veterinary use as well as human pharmaceutical use. A "pharmaceutically acceptable carrier" includes both one and more than one such carrier.

A "patient" means a human or non-human animal in need of medical treatment. Medical treatment can include treatment of an existing condition, such as a disease or disorder or diagnostic treatment. In some embodiments the patient is a human patient.

"Providing" means giving, administering, selling, distributing, transferring (for profit or not), manufacturing, compounding, or dispensing.

"Treatment" or "treating" means providing an active compound to a patient in an amount sufficient to measurably reduce any cancer symptom, slow cancer progression or cause cancer regression. In certain embodiments treatment of the cancer may be commenced before the patient presents symptoms of the disease.

A "therapeutically effective amount" of a pharmaceutical composition means an amount effective, when administered to a patient, to provide a therapeutic benefit such as an amelioration of symptoms, decrease cancer progression, or cause cancer regression.

A significant change is any detectable change that is statistically significant in a standard parametric test of statistical significance such as Student's T-test, where $p < 0.05$.

Chemical Description

Compounds of Formula I may contain one or more asymmetric elements such as stereogenic centers, stereogenic axes and the like, e.g., asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, all optical isomers in pure form and mixtures thereof are encompassed. In these situations, the single enantiomers, i.e., optically active forms can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column. All forms are contemplated herein regardless of the methods used to obtain them.

All forms (for example solvates, optical isomers, enantiomeric forms, polymorphs, free compound and salts) of an active agent may be employed either alone or in combination.

The term "chiral" refers to molecules, which have the property of non-superimposability of the mirror image partner.

"Stereoisomers" are compounds, which have identical chemical constitution, but differ with regard to the arrangement of the atoms or groups in space.

A "diastereomer" is a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis, crystallization in the presence of a resolving agent, or chromatography, using, for example a chiral HPLC column.

"Enantiomers" refer to two stereoisomers of a compound, which are non-superimposable mirror images of one another. A 50:50 mixture of enantiomers is referred to as a racemic mixture or a racemate, which may occur where there has been no stereoselection or stereospecificity in a chemical reaction or process.

Stereochemical definitions and conventions used herein generally follow S. P. Parker, Ed., McGraw-Hill *Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and 1 or (+) and (−) are employed to designate the sign of rotation of plane-polarized light by the compound, with (−) or 1 meaning that the compound is levorotatory. A compound prefixed with (+) or d is dextrorotatory.

A "racemic mixture" or "racemate" is an equimolar (or 50:50) mixture of two enantiomeric species, devoid of optical activity. A racemic mixture may occur where there has been no stereoselection or stereospecificity in a chemical reaction or process.

"Pharmaceutically acceptable salts" include derivatives of the disclosed compounds in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media such as ether, ethyl acetate, ethanol, isopropanol, or acetonitrile are used, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like. Lists of additional suitable salts may be found, e.g., in G. Steffen Paulekuhn, et al., *Journal of Medicinal Chemistry* 2007, 50, 6665 and *Handbook of Pharmaceutically Acceptable Salts: Properties, Selection and Use*, P. Heinrich Stahl and Camille G. Wermuth, Editors, Wiley-VCH, 2002.

TDP2 Inhibitors

Molecules which inhibit TDP2 are disclosed herein.

In addition to compounds of Formula I shown in the SUMMARY section, the disclosure also includes compounds in which the variables, e.g. A, B, $X^1$, $X^2$, W, Y, Z, $R^1$ to $R^{10}$ carry the following definitions. The disclosure includes all combinations of these definitions so long as a stable compound results. The disclosure includes the following particular embodiments of Formula (I).

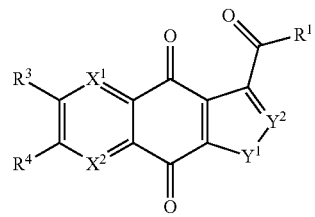

Formula I

The disclosure includes compounds of Formula IA and IB and salts thereof.

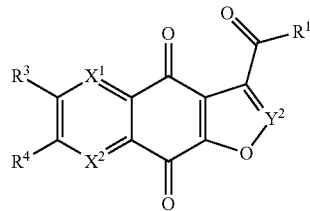

Formula IA

Formula IB

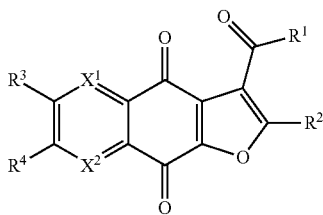

$R^1$ is hydroxyl, $C_1$-$C_8$alkoxy or —O—($C_0$-$C_6$alkyl)cycloalkyl, in which one or more methylene units in the alkoxy or alkyl portion of $R^1$ is optionally and independently replaced with —O— or —N($R^7$)—, and $R^1$ is substituted by 0-3 substituents independently chosen at each occurrence from hydroxyl, halogen, cyano, —$CO_2H$, —(CO)—O—$C_1$-$C_6$alkyl, and —W—P(O)$YR^9ZR^{10}$; or $R^1$ is —O-A-B.

B is a phenyl, or a 5 or 6 membered heteroaryl having 1, 2, or 3 Nitrogen ring atoms, wherein B is optionally substituted with 0-3 substituents independently chosen from halogen, hydroxyl, cyano, amino, $C_1$-$C_6$alkyl, $C_2$-$C_6$alkenyl, $C_2$-$C_6$alkynyl, $C_2$-$C_6$alkanoyl, $C_1$-$C_6$alkoxy, $C_1$-$C_6$haloalkyl, $C_1$-$C_6$haloalkoxy, —($C_0$-$C_6$alkyl)cycloalkyl, —($C_0$-$C_6$alkyl)$CO_2H$, —($C_0$-$C_6$alkyl)-(CO)—O—$C_1$-$C_6$alkyl, —($C_1$-$C_6$alkyl)alkoxy, —($C_1$-$C_6$alkyl)OH, —$SO_2$—$C_1$-$C_6$alkyl, and —($C_0$-$C_6$alkyl)-W—P(O)$YR^9ZR^{10}$.

$R^2$ is halogen, $C_1$-$C_6$alkyl, $C_1$-$C_6$haloalkyl, or —($C_0$-$C_6$alkyl)cycloalkyl, or phenyl, said phenyl being substituted with 0 to 3 groups chosen independently at each occurrence from halogen, hydroxyl, $C_1$-$C_6$alkyl, $C_1$-$C_6$alkoxy, $C_1$-$C_6$haloalkyl, and $C_1$-$C_6$haloalkoxy.

(B) $R^3$ and $R^4$ are both hydrogen.

(C) $R^2$ is $C_1$-$C_6$alkyl, $C_1$-$C_6$haloalkyl, —($C_0$-$C_6$alkyl)cycloalkyl, or phenyl, said phenyl being substituted with 0 to 3 groups chosen independently at each occurrence from halogen, hydroxy, $C_1$-$C_6$alkyl, $C_1$-$C_6$alkoxy, $C_1$-$C_6$haloalkyl, and $C_1$-$C_6$haloalkoxy. (D) $R^1$ is substituted with at least one —W—P(O)$YR^9ZR^{10}$ substituent; and W is a bond, and Y and Z are both 0.

(E) $R^2$ is methyl or phenyl.

(F) $X^1$ is N and $X^2$ is CH.

(G) $X^1$ is CH and $X^2$ is N.

(H) $R^1$ is $C_1$-$C_8$alkoxy.

$R^1$ is a phenoxy or pyridyloxy, each of which is optionally substituted with 0-3 substituents independently chosen from halogen, hydroxyl, cyano, $C_1$-$C_6$alkyl, $C_2$-$C_6$alkenyl, $C_2$-$C_6$alkynyl, $C_1$-$C_6$alkoxy, $C_1$-$C_6$haloalkyl, $C_1$-$C_6$haloalkoxy, —($C_0$-$C_6$alkyl)cycloalkyl, —($C_0$-$C_6$alkyl)$CO_2H$, —($C_0$-$C_6$alkyl)-(CO)—O—$C_1$-$C_6$alkyl, —($C_1$-$C_6$alkyl)alkoxy, —($C_1$-$C_6$alkyl)OH, —$SO_2$—$C_1$-$C_6$alkyl, and —($C_0$-$C_6$alkyl)-W—P(O)$YR^9ZR^{10}$.

(I) $R^1$ is alkoxy where one or more methylene units in the alkyl portion of $R^1$ is optionally replaced by —O— or —N($R^7$)— and $R^1$ is substituted with 1 to 3 substituents independently chosen from hydroxyl and —WP(O)$YR^9ZR^{10}$; where W is a bond; and Y and Z are both 0.

(J) $R^1$ is —O-A-B.

(K) $R^1$ is —O-A-B;

A is a bond or an alkylene chain of 1 to 3 carbon atoms; and

B is phenyl or pyridyl optionally substituted with 0-3 substituents independently chosen from halogen, hydroxyl, cyano, $C_1$-$C_4$alkyl, $C_1$-$C_4$alkoxy, $C_2$-$C_4$alkanoyl, $C_1$-$C_2$haloalkyl, $C_1$-$C_2$haloalkoxy, —($C_0$-$C_2$alkyl)-(CO)—O—$C_1$-$C_6$alkyl, —($C_0$-$C_2$alkyl)C(O)$NR^7R^8$, —($C_0$-$C_2$alkyl)$NR^7C(O)R^8$, —($C_1$-$C_6$alkyl)OH, and —$SO_2$—$C_1$-$C_2$alkyl.

(L) $R^1$ is —O-A-B;

A is a bond; and

B is phenyl substituted with one substituent chosen from hydroxyl, halogen, and cyano.

(M) $R^1$ is —O-A-B; and

B is a triazolyl, pyrazolyl, imidazolyl, thienyl, dioxylanyl, morpholinyl, piperazinyl, or piperidinyl group; each of which B is substituted with 0-3 substituents independently chosen from halogen, hydroxyl, cyano, amino, $C_1$-$C_6$alkyl, $C_2$-$C_6$alkenyl, $C_2$-$C_6$alkynyl, $C_1$-$C_6$alkoxy, $C_2$-$C_6$alkanoyl, $C_1$-$C_2$haloalkyl, $C_1$-$C_2$haloalkoxy, —($C_0$-$C_6$alkyl)$CO_2H$, —($C_0$-$C_6$alkyl)-(CO)—O—$C_1$-$C_6$alkyl, —($C_0$-$C_6$alkyl)C(O)$NR^7R^8$, —($C_0$-$C_6$alkyl)$NR^7C(O)R^8$, —($C_1$-$C_6$alkyl)OH, —($C_0$-$C_6$alkyl)$NR^7R^8$, and —$SO_2$—$C_1$-$C_6$alkyl; where $R^7$ and $R^8$ are hydrogen or $C_1$-$C_4$alkyl.

(N) $R^2$ is hydrogen, halogen, $C_1$-$C_6$alkyl, $C_1$-$C_6$alkoxy, $C_1$-$C_6$haloalkyl, $C_1$-$C_6$haloalkoxy, —($C_0$-$C_6$alkyl)cycloalkyl, —($C_0$-$C_6$alkyl)$NR^7R^8$, or phenyl, each $R^2$ other than hydrogen and halogen being substituted with 0 to 3 groups chosen independently at each occurrence from halogen, hydroxyl, $C_1$-$C_6$alkyl, $C_1$-$C_6$alkoxy, $C_1$-$C_6$haloalkyl, and $C_1$-$C_6$haloalkoxy.

(O) $R^2$ is

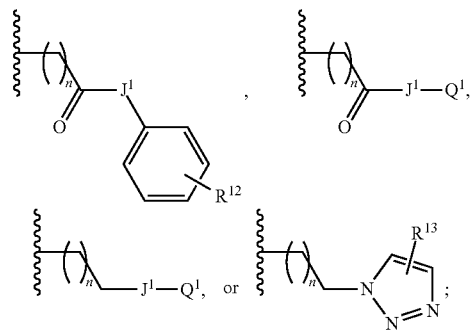

where n is 1, 2, 3, or 4;

$J^1$ is O, NH, $NR^{11}$;

$Q^1$ is $C_1$-$C_6$alkyl, or $C_1$-$C_6$alkylamino-;

$R^{12}$ is absent or 1 or more substituents independently chosen from hydroxyl, halogen, amino, or cyano; and $R^{13}$ is absent or 1 or 2 substituents independently chosen from $C_1$-$C_4$alkyl, and mono- or di-$C_1$-$C_6$alkylamino.

The disclosure includes an embodiment which is a pharmaceutical composition comprising a compound or salt of Formula I, together with a pharmaceutically acceptable carrier.

Pharmaceutical Preparations

Compounds disclosed herein can be administered as the neat chemical, but are preferably administered as a pharmaceutical composition. Accordingly, the disclosure provides pharmaceutical compositions comprising a compound or pharmaceutically acceptable salt of a Tdp1 inhibitor, such as a compound of Formula I, together with at least one pharmaceutically acceptable carrier. The pharmaceutical composition/combination may contain a compound or salt of Formula I as the only active agent, but is preferably contains at least one additional active agent. In certain embodiments it is preferred that the additional active agent is compound or salt thereof chosen from camptothecin, irinotecan, and topotecan. In certain embodiments the additional active agent is etoposide, teniposide, doxorubicin, daunorubicin, mitoxantrone, amsacrine, ellipticines, aurintricarboxylic acid, and 3-hydroxy-2-[(1R)-6-isopropenyl-3-methyl-cyclohex-2-en-1-yl]-5-pentyl-1,4-benzoquinone (HU-331). In certain embodiments the pharmaceutical composition is in a dosage form that contains from about 0.1 mg to about 2000 mg, from about 10 mg to about 1000 mg, from about 100 mg to about 800 mg, or from about 200 mg to about 600 mg of a compound of Formula I and optionally from about 0.1 mg to about 2000 mg, from about 10 mg to about 1000 mg, from about 100 mg to about 800 mg, or from about 200 mg to about 600 mg of an additional active agent in a unit dosage form. The pharmaceutical composition may also include a molar ratio of a compound of Tdp1 inhibitor, such as a compound of Formula I, and an additional active agent. For example the pharmaceutical composition may contain a molar ratio of about 0.5:1, about 1:1, about 2:1, about 3:1 or from about 1.5:1 to about 4:1 of an TDP2 inhibitor of Formula I to additional active agent.

Compounds disclosed herein may be administered orally, topically, parenterally, by inhalation or spray, sublingually, transdermally, via buccal administration, rectally, as an ophthalmic solution, or by other means, in dosage unit formulations containing conventional pharmaceutically acceptable carriers. The pharmaceutical composition may be formulated as any pharmaceutically useful form, e.g., as an aerosol, a cream, a gel, a pill, a capsule, a tablet, a syrup, a transdermal patch, or an ophthalmic solution. Some dosage forms, such as tablets and capsules, are subdivided into suitably sized unit doses containing appropriate quantities of the active components, e.g., an effective amount to achieve the desired purpose.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, flavorants, glidants, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Optional active agents may be included in a pharmaceutical composition, which do not substantially interfere with the activity of the compound of the present invention.

The pharmaceutical compositions/combinations can be formulated for oral administration. These compositions contain between 0.1 and 99 weight % (wt. %) of a compound of Formula I and usually at least about 5 wt. % of a compound of Formula I. Some embodiments contain from about 25 wt. % to about 50 wt. % or from about 5 wt. % to about 75 wt. % of the compound of Formula I.

Treatment Methods

The compounds of Formula I or a salt thereof, as well as pharmaceutical compositions comprising the compounds, are useful for treating cancer, including effecting tumor regression in vivo. The method of treating cancer or effecting tumor regression comprises providing to a patient in need of such treatment a therapeutically effective amount of a compound of Formula I. In an embodiment the patient is a mammal, and more specifically a human. The disclosure also provides methods of treating non-human patients such as companion animals, e.g. cats, dogs, and livestock animals. A therapeutically effective amount of a pharmaceutical composition may be an amount sufficient to inhibit the progression of cancer or a cancerous tumor; or cause a regression of a cancer or a cancerous tumor.

A therapeutically effective amount of a compound or pharmaceutical composition described herein will also provide a sufficient concentration of a compound of Formula I when administered to a patient. A sufficient concentration is a concentration of the compound in the patient's body necessary to prevent or combat the disorder. Such an amount may be ascertained experimentally, for example by assaying blood concentration of the compound, or theoretically, by calculating bioavailability.

Methods of treatment include providing certain dosage amounts of a compound of Formula I to a patient. Dosage levels of each compound of from about 0.1 mg to about 140 mg per kilogram of body weight per day are useful in the treatment of the above-indicated conditions (about 0.5 mg to about 7 g per patient per day). The amount of compound that may be combined with the carrier materials to produce a single dosage form will vary depending upon the patient treated and the particular mode of administration. Dosage unit forms will generally contain between from about 1 mg to about 500 mg of each active compound. In certain embodiments 25 mg to 500 mg, or 25 mg to 200 mg of a compound of Formula I are provided daily to a patient. Frequency of dosage may also vary depending on the compound used and the particular disease treated. However, for treatment of most diseases and disorders, a dosage regimen of 4 times daily or less can be used and in certain embodiments a dosage regimen of 1 or 2 times daily is used.

The compounds of Formula I may be used to treat cancers and effect regression of tumors, including cancerous tumors. In certain embodiments, the patient is suffering from a cell proliferative disorder or disease. The cell proliferative disorder can be cancer, tumor (cancerous or benign), neoplasm, neovascularization, or melanoma. Cancers for treatment include both solid and disseminated cancers. Exemplary solid cancers (tumors) that may be treated by the methods provided herein include e.g. cancers of the lung, prostate, breast, liver, colon, breast, kidney, pancreas, brain, skin including malignant melanoma and Kaposi's sarcoma, testes or ovaries, carcinoma, sarcoma, and kidney cancer (renal cell). Cancers that may be treated with a compound of Formula I also include bladder cancer, breast cancer, colon cancer, endometrial cancer, lung cancer, bronchial cancer, melanoma, Non-Hodgkins lymphoma, cancer of the blood, pancreatic cancer, prostate cancer, thyroid cancer, brain or spinal cancer, and leukemia. Exemplary disseminated cancers include leukemias or lymphoma including Hodgkin's disease, multiple myeloma and mantle cell lymphoma (MCL), chronic lymphocytic leukemia (CLL), T-cell leukemia, multiple myeloma, and Burkitt's lymphoma. Particularly included herein are methods of treating cancer by providing a compound of Formula I to a patient wherein the cancer is a solid tumor or disseminated cancer.

Further included are methods of treating cancer by providing a compound of Formula I to a patient wherein the cancer is selected from glioma (glioblastoma), acute myelogenous leukemia, acute myeloid leukemia, myelodysplastic/myeloproliferative neoplasms, sarcoma, chronic myelomonocytic leukemia, non-Hodgkin's lymphoma, astrocytoma, melanoma, non-small cell lung cancer, small cell lung cancer, cervical cancer, rectal cancer, ovarian cancer, cholangiocarcinomas, chondrosarcoma, or colon cancer.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy A compound of Formula I may be administered singularly (i.e., sole therapeutic agent of a regime) to treat or prevent diseases and conditions such as undesired cell proliferation, cancer, and/or tumor growth or may be administered in combination with another active agent. One or more compounds of Formula I may be administered in coordination with a regime of one or more other chemotherapeutic agents such as an antineoplastic drug, e.g., an alkylating agent (e.g., mechloroethamine, chlorambucil, cyclophosamide, melphalan, or ifosfamide), an antimetabolite such as a folate antagonist (e.g., methotrexate), a purine antagonist (e.g. 6-mercaptopurine), or a pyrimidine antagonist (e.g., 5-fluorouracil). Other, non-limiting examples of chemotherapeutic agents that might be used in coordination with one or more compounds of Formula I include taxanes and topoisomerase inhibitors. In addition, other non-limiting examples of active therapeutics include biological agents, such as monoclonal antibodies or IgG chimeric molecules, that achieve their therapeutic effect by specifically binding to a receptor or ligand in a signal transduction pathway associated with cancer (e.g. therapeutic antibodies directed against CD20 (e.g. rituximab) or against VEGF (e.g. bevacizumab)).

Methods of treatment provided herein are also useful for treatment of mammals other than humans, including for veterinary applications such as to treat horses and livestock, e.g. cattle, sheep, cows, goats, swine and the like, and pets (companion animals) such as dogs and cats.

For diagnostic or research applications, a wide variety of mammals will be suitable subjects including rodents (e.g. mice, rats, hamsters), rabbits, primates, and swine such as inbred pigs and the like. Additionally, for in vitro applications, such as in vitro diagnostic and research applications, body fluids (e.g. blood, plasma, serum, cellular interstitial fluid, saliva, feces, and urine) and cell and tissue samples of the above subjects will be suitable for use.

In an embodiment, the invention provides a method of treating a cancer disorder in a patient identified as in need of such treatment, the method comprising providing to the patient an effective amount of a compound of Formula I. The compounds and salts of Formula I provided herein may be administered alone, or in combination with one or more other active agents.

In an embodiment, the method of treating cancer may additionally comprise determining the cancer responds to Tdp2 inhibition.

In an embodiment, the method of treating cancer may additionally comprise administering the compound of Formula I in combination with one or more additional compounds, wherein at least one of the additional compounds is an active agent known to be an inhibitor of topoisomerase 2, to a patient in need of such treatment.

In an embodiment, the method of treating cancer may additionally comprise administering a therapeutically effective amount of a compound or salt of Formula I, in combination with one or more additional compounds, wherein at least one additional compound is an active agent chosen from etoposide, teniposide, doxorubicin, daunorubicin, mitoxantrone, amsacrine, ellipticines, aurintricarboxylic acid, and 3-hydroxy-2-[(1R)-6-isopropenyl-3-methyl-cyclohex-2-en-1-yl]-5-pentyl-1,4-benzoquinone (HU-331), to a patient in need of such treatment.

In other embodiments, the cancer is one which can be treated with Top2 inhibitors, wherein TDP2 inhibitors may provide synergistic effects as a combination therapy with inhibitors of Top2, such as etoposide and doxorubicin.

EXAMPLES

Abbreviations

DCM Dichloromethane
DMF N,N-Dimethylformamide
DMSO Dimethyl Sulfoxide
DTT Dithiothreitol
EDTA Ethylenediaminetetraacetic acid
ESI Electrospray Ionization
HPLC High Performance Liquid Chromatography
HRMS High Resolution Mass Spectrometry
NMR Nuclear Magnetic Resonance
THF Tetrahydrofuran
WCE Whole Cell Extract General Methods The reagents and solvents used were commercial anhydrous grade. They were used without further purification if not mentioned. Column chromatography was carried out over silica gel (200-300 mesh). $^1$H NMR spectra were recorded on a Bruker AVANCE III 400 MHz spectrometer using tetramethylsilane as an internal reference. Mass spectra were analyzed on an Agilent 6120 (Quadrupole LCMS) mass spectrometer. The high-resolution mass spectra were analyzed on a SHIMADZU LCMS-IT-TOF mass spectrometer. The HPLC analytical method employed a SHIMADZU LC-20AB Liquid Chromatography system with SPD-M20A detector. The analytical method conditions included a Phenomenex C18 column (4.6×250 mm, 5.0 um) and elution with a linear gradient of 25% methanol in pH 3.0 buffered aqueous NaH$_2$PO$_4$ to 75% methanol at 1 mL/min flow rate. The purity was determined using UV peak area at 220 nm. HPLC method A used a buffer of H$_2$O with 0.1% TFA, method B used a buffer of phosphate buffered saline at pH 6, method C used a buffer of phosphate buffered saline at pH 3.

Examples

The following scheme provides a general method for preparing compounds of Formula I

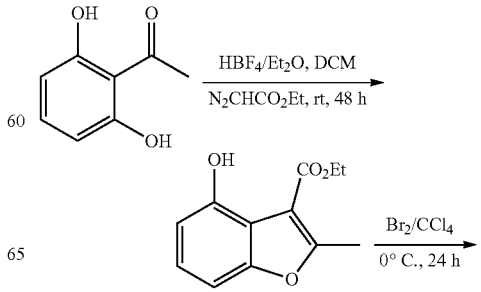

room temperature, and concentrated under reduced pressure. The target products were purified by silica gel column chromatography.

Ethyl 2-methyl-4,9-dioxo-4,9-dihydrofuro[3,2-g]quinoline-3-carboxylate (1), yellow solid. $^1$H NMR (400 MHz, CDCl$_3$) δ 9.04 (d, J=4.8 Hz, 1H), 8.54 (d, J=8.0 Hz, 1H), 7.67 (dd, J=7.6, 4.7 Hz, 1H), 4.46 (q, J=7.1 Hz, 2H), 2.76 (s, 3H), 1.46 (t, J=6.7 Hz, 3H). HRMS (ESI) m/z: 284.0574 [M-H]$^-$, calcd for C$_{15}$H$_{10}$NO$_5$ 284.0564.

Ethyl 2-methyl-4,9-dioxo-4,9-dihydrofuro[2,3-g]quinoline-3-carboxylate (2), yellow solid. $^1$H NMR (400 MHz, CDCl$_3$) δ 9.06 (d, J=4.0 Hz, 1H), 8.54 (d, J=7.6 Hz, 1H), 7.70 (dd, J=7.6, 4.7 Hz, 1H), 4.44 (q, J=6.7 Hz, 2H), 2.76 (s, 3H), 1.48 (t, J=7.2 Hz, 3H). HRMS (ESI) m/z: 284.0551 [M-H]$^-$, calcd for C$_{15}$H$_{10}$NO$_5$ 284.0564.

Example 2. Synthesis of Compounds 8 and 9

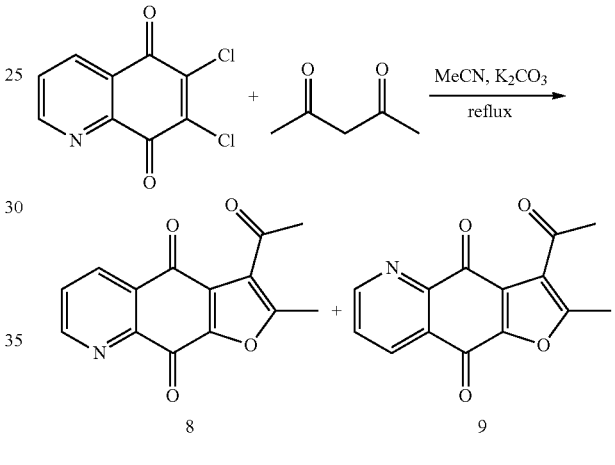

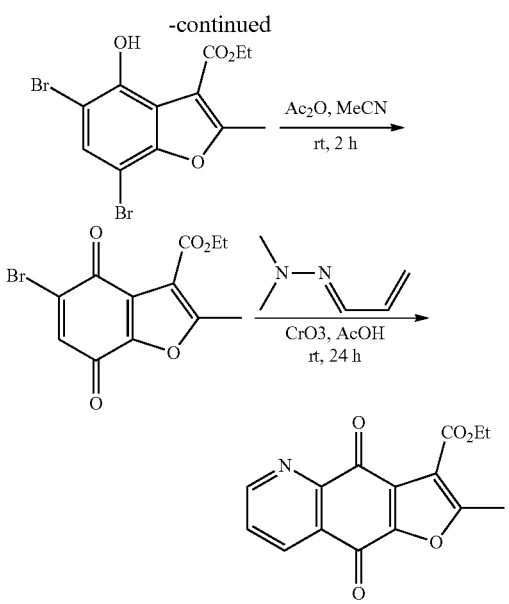

Example 1. Synthesis of Compounds 1 and 2

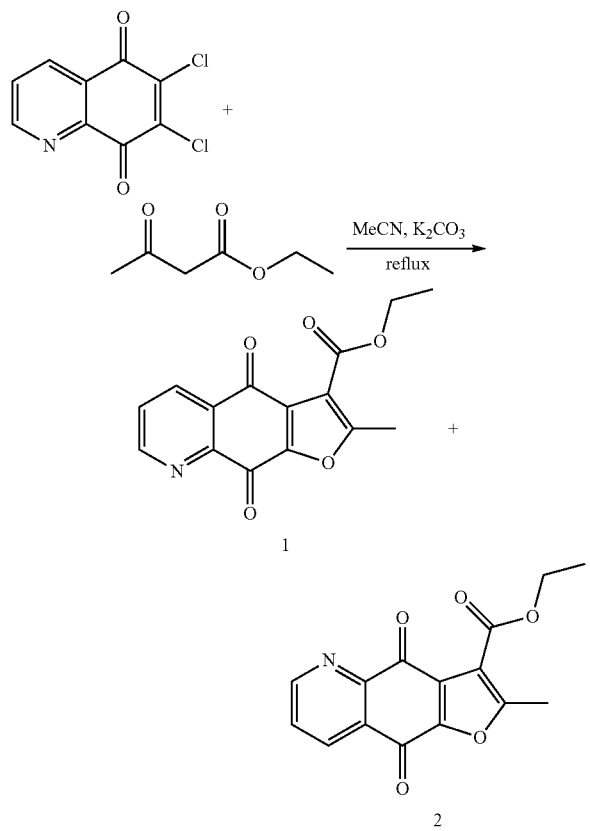

To a yellow solution of 6,7-dichloroquinoline-5,8-dione (0.46 g, 2 mmol) in MeCN (30 ml), ethyl acetoacetate (0.26 ml, 2.2 mmol) and K$_2$CO$_3$ (1.10 g, 8 mmol) were added. The resultant solution was stirred and refluxed for 6 h. After completion of reaction, the reaction solution was cooled to According to Preparation 1, using acetylacetone as material to give the target products 8 and 9.

3-acetyl-2-methylfuro[3,2-g]quinoline-4,9-dione (8), yellow solid. $^1$H NMR (400 MHz, CDCl$_3$) δ 9.07 (dd, J=4.7, 1.7 Hz, 1H), 8.54 (dd, J=7.9, 1.7 Hz, 1H), 7.73 (dd, J=7.9, 4.7 Hz, 1H), 2.79 (s, 3H), 2.70 (s, 3H). HRMS (ESI) m/z: 256.0593 [M+H]$^+$, calcd for C$_{14}$H$_{10}$NO$_4$ 256.0604.

3-acetyl-2-methylfuro[2,3-g]quinoline-4,9-dione (9), yellow solid. $^1$H NMR (400 MHz, CDCl$_3$) δ 9.07 (d, J=4.5 Hz, 1H), 8.55 (dd, J=7.8, 1.2 Hz, 1H), 7.73 (dd, J=7.8, 4.7 Hz, 1H), 2.81 (s, 3H), 2.70 (s, 3H)$_o$ HRMS (ESI) m/z: 256.0613 [M+H]$^+$, calcd for C$_{14}$H$_{10}$NO$_4$ 256.0604.

Example 3. Synthesis of Compound 3

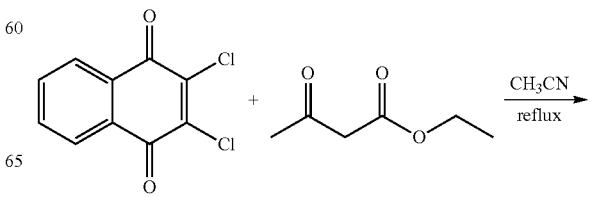

-continued

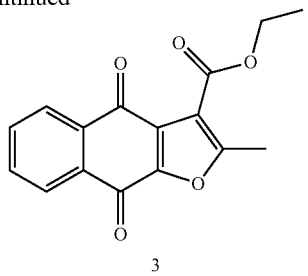

3

According to Preparation 1, using 2,3-dichloronaphthalene-1,4-dione as material to give the target product 3 (Ethyl 2-methyl-4,9-dioxo-4,9-dihydronaphtho[2,3-b]furan-3-carboxylate), yellow solid. $^1$H NMR (400 MHz, CDCl$_3$) δ 8.23-8.16 (m, 2H), 7.76-7.74 (m, 2H), 4.45 (q, J=7.1 Hz, 1H), 2.72 (s, 3H), 1.45 (t, J=7.1 Hz, 3H). HRMS (ESI) m/z: 307.0590 [M+Na]$^+$, calcd for C$_{16}$H$_{12}$O$_5$Na 307.0577.

Example 4. Synthesis of Compounds 29 and 30

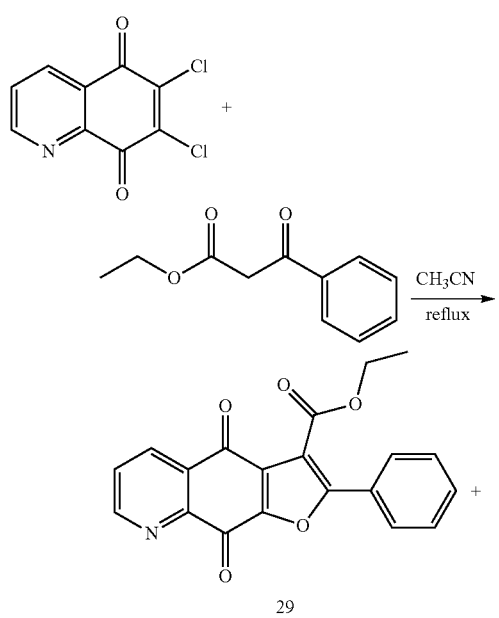

According to Preparation 1, using ethyl 3-oxo-3-phenyl-propanoate as material to give the target products 29 and 30.

Ethyl 4,9-dioxo-2-phenyl-4,9-dihydrofuro[3,2-g]quinoline-3-carboxylate (29), yellow solid. $^1$H NMR (400 MHz, CDCl$_3$) δ 9.08 (dd, J=4.6, 1.6 Hz, 1H), 8.53 (dd, J=7.9, 1.6 Hz, 1H), 8.21-7.84 (m, 2H), 7.72 (dd, J=7.9, 4.7 Hz, 1H), 7.60-7.42 (m, 3H), 4.51 (q, J=7.1 Hz, 2H), 1.43 (t, J=7.1 Hz, 3H). HRMS (ESI) m/z: 348.0865 [M+H]$^+$, calcd for C$_{20}$H$_{14}$NO$_5$ 348.0866.

Ethyl 4,9-dioxo-2-phenyl-4,9-dihydrofuro[2,3-g]quinoline-3-carboxylate (30), yellow solid. $^1$H NMR (400 MHz, CDCl$_3$) δ 9.06 (dd, J=4.7, 1.7 Hz, 1H), 8.58 (dd, J=7.9, 1.7 Hz, 1H), 8.00-7.95 (m, 2H), 7.72 (dd, J=7.9, 4.7 Hz, 1H), 7.52-7.49 (m, 3H), 4.53 (q, J=7.1 Hz, 2H), 1.46 (t, J=7.1 Hz, 3H). HRMS (ESI) m/z: 348.0887 [M+H]$^+$, calcd for C$_{20}$H$_{14}$NO$_5$ 348.0866.

Example 5. Preparation 2: Synthesis of Compound 7

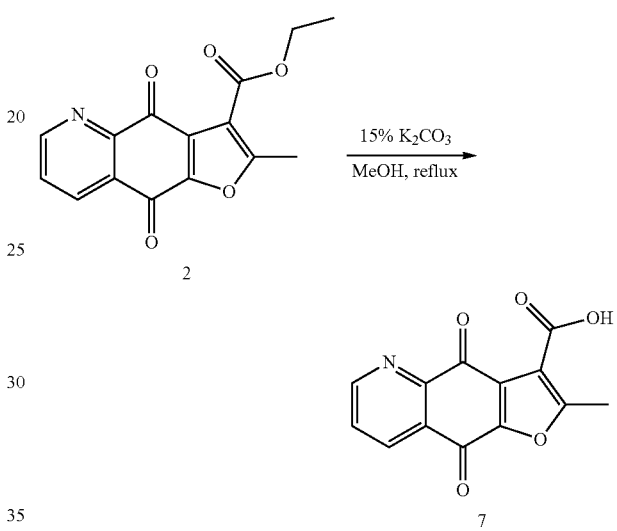

To the solution of 2 (1.10 g, 4 mmol) in MeOH or iso-propanol (300 ml), aqueous solution of K$_2$CO$_3$ (15%, 30 ml) was added. The reaction solution was refluxed for 12 h. The precipitate was filtered and dissolved in water (500 ml). The aqueous solution was acidized to pH 3 with hydrochloric acid (2 N), and extracted with DCM (100 ml×3). The organic solution was dried with anhydrous MgSO$_4$ and concentrated under reduced pressure. The resultant solid was recrystallized in MeOH to give the target compound yellow solid 7.

2-methyl-4,9-dioxo-4,9-dihydrofuro[2,3-g]quinoline-3-carboxylic acid (7). $^1$H NMR (400 MHz, CDCl$_3$) δ 9.12 (dd, J=4.7, 1.7 Hz, 1H), 8.59 (dd, J=7.9, 1.7 Hz, 1H), 7.82 (dd, J=7.9, 4.7 Hz, 1H), 2.93 (s, 3H).

Example 6. Preparation 3: Synthesis of Compound 10

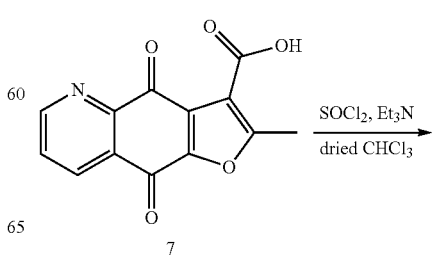

7

-continued

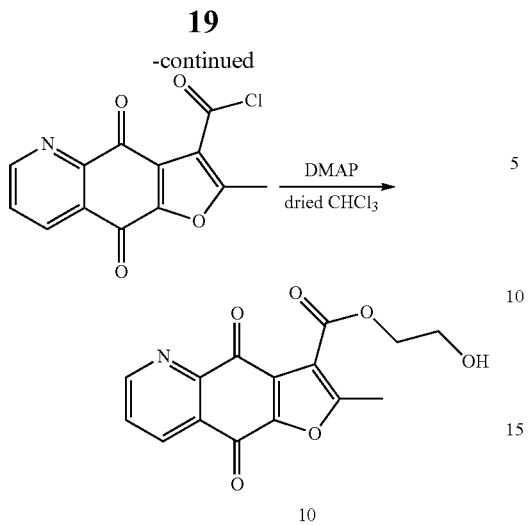

At room temperature, to a red solution of compound 7 (65 mg, 0.25 mmol) and triethylamine (0.07 ml, 0.5 mmol) in new distilled chloroform (20 ml), thionyl chloride (1.25 ml) was added dropwise. The mixture was stirred and refluxed for 5 h. The reaction solution was then cooled to room temperature. The solvent was evaporated under reduced pressure. The residue was contained under reduced pressure for a period to get rid of most of the residual thionyl chloride to give an orange solid residue. The resultant residue was dissolved in new distilled chloroform (10 ml), and added dropwise to a solution of 4-(Dimethylamino)pyridine (35 mg, 0.3 mmol) and ethanediol (0.3 mmol) in new distilled chloroform (30 ml). The reaction mixture was refluxed for 3 h, and cooled to room temperature. The solvent was evaporated under reduced pressure. The target product was purified by silica gel column chromatography.

2-hydroxyethyl-2-methyl-4,9-dioxo-4,9-dihydrofuro[2,3-g]quinoline-3-carboxylate (10), yellow solid. $^1$H NMR (400 MHz, CDCl$_3$) δ 9.08 (d, J=3.2 Hz, 1H), 8.56 (d, J=7.6 Hz, 1H), 7.73 (dd, J=7.4, 4.4 Hz, 1H), 4.49 (t, J=4.4 Hz, 2H), 4.00 (t, J=4.4 Hz, 2H), 2.80 (s, 3H). HRMS (ESI) m/z: 300.0499 [M−H]$^-$, calcd for C$_{15}$H$_{10}$NO$_6$ 300.0514.

Example 7. Synthesis of Compound 11

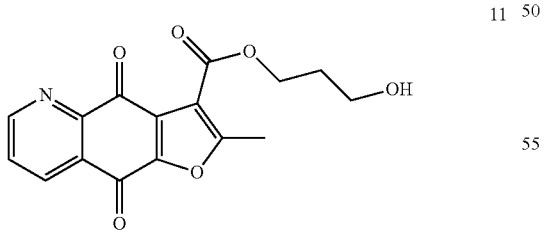

According to Preparation 3, using propanediol as material to give the target yellow solid 11. $^1$H NMR (400 MHz, CDCl$_3$) δ 9.06 (d, J=3.3 Hz, 1H), 8.54 (d, J=7.0 Hz, 1H), 7.71 (dd, J=7.6, 4.7 Hz, 1H), 4.55 (t, J=5.9 Hz, 2H), 3.91 (t, J=5.9 Hz, 2H), 2.77 (s, 3H), 2.09 (quint, J=5.8 Hz, 2H). HRMS (ESI) m/z: 314.0653 [M−H]$^-$, calcd for C$_{16}$H$_{12}$NO$_6$ 314.0670.

Example 8 Synthesis of Compound 12

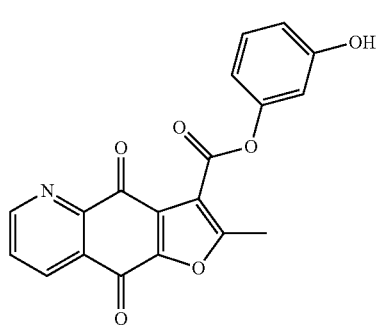

According to Preparation 3, using m-dihydroxybenzene as material to give the target yellow solid 12. $^1$H NMR (400 MHz, DMSO) δ 9.81 (s, 1H), 9.03 (d, J=3.1 Hz, 1H), 8.49 (d, J=7.2 Hz, 1H), 7.87 (dd, J=6.6, 4.9 Hz, 1H), 7.31-7.26 (m, 1H), 6.88-6.68 (m, 3H), 2.76 (s, 3H). HRMS (ESI) m/z: 348.0499 [M−H]$^-$, calcd for C$_{19}$H$_{10}$NO$_6$ 348.0514.

Example 9. Synthesis of Compound 13

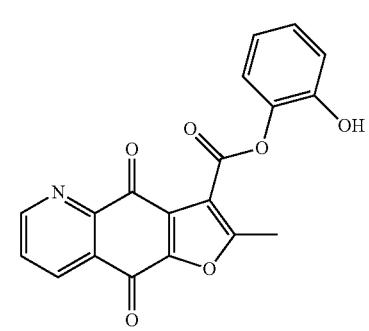

According to Preparation 3, using o-dihydroxybenzene as material to give the target yellow solid 13. $^1$H NMR (400 MHz, DMSO) δ 9.81 (s, 1H), 9.03 (d, J=3.9 Hz, 1H), 8.49 (d, J=7.7 Hz, 1H), 7.87 (dd, J=7.6, 4.7 Hz, 1H), 7.23 (d, J=7.8 Hz, 1H), 7.16 (t, J=7.6 Hz, 1H), 7.00 (d, J=7.9 Hz, 1H), 6.90 (t, J=7.5 Hz, 1H), 2.80 (s, 3H). HRMS (ESI) m/z: C$_{19}$H$_{10}$NO$_6$ 348.0514 calcd for 348.0512.

Example 10. Synthesis of Compound 14

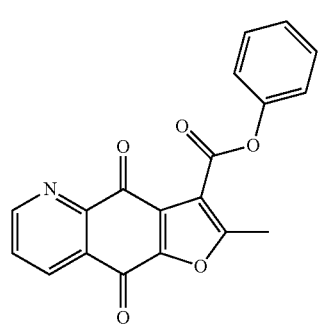

According to Preparation 3, using phenol as material to give the target yellow solid 14. $^1$H NMR (400 MHz, DMSO) δ 9.03 (dd, J=4.7, 1.7 Hz, 1H), 8.49 (dd, J=7.9, 1.7 Hz, 1H), 7.87 (dd, J=7.9, 4.7 Hz, 1H), 7.62-7.46 (m, 2H), 7.44-7.29

(m, 3H), 2.78 (s, 3H). HRMS (ESI) m/z: 332.0563 [M−H]⁻, calcd for C$_{19}$H$_{10}$NO$_5$ 332.0564.

Example 11. Synthesis of Compound 15

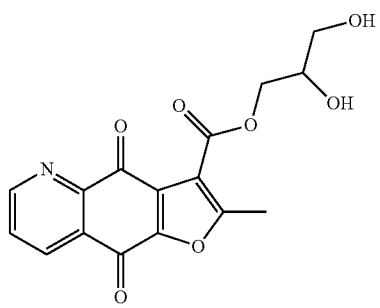

15

According to Preparation 3, using phenol as material to give the target yellow solid 15. $^1$H NMR (400 MHz, CDCl$_3$) δ 9.08 (dd, J=4.7, 1.7 Hz, 1H), 8.55 (dd, J=7.9, 1.7 Hz, 1H), 7.73 (dd, J=7.9, 4.7 Hz, 1H), 4.47 (d, J=5.2 Hz, 2H), 4.19-4.17 (m, 1H), 3.83-3.74 (m, 2H), 2.80 (s, 3H). HRMS (ESI) m/z: 330.0604 [M−H]⁻, calcd for C$_{16}$H$_{12}$NO$_7$ 330.0619.

Example 12. Synthesis of Compound 16

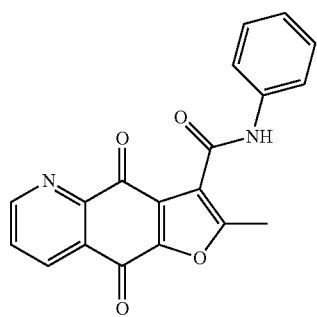

16

According to Preparation 3, using phenylamine as material to give the target yellow solid 16. $^1$H NMR (400 MHz, DMSO) δ 11.10 (s, 1H), 9.06 (d, J=3.2 Hz, 1H), 8.51 (dd, J=7.8, 1.5 Hz, 1H), 7.91 (dd, J=7.7, 4.7 Hz, 1H), 7.77-7.75 (m, 2H), 7.44-7.40 (m, 2H), 7.18-7.14 (m, 1H), 2.78 (s, 3H). HRMS (ESI) m/z: 331.0723 [M−H]⁻, calcd for C$_{19}$H$_{11}$N$_2$O$_4$ 331.0724.

Example 13. Synthesis of Compound 17

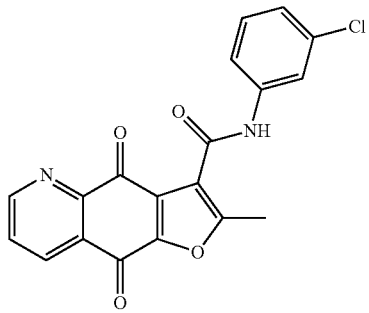

17

According to Preparation 3, using m-chlorophenylamine as material to give the target yellow solid 17. $^1$H NMR (400 MHz, DMSO) δ 11.19 (s, 1H), 9.07 (d, J=3.2 Hz, 1H), 8.51 (dd, J=7.8, 1.5 Hz, 1H), 7.96 (s, 1H), 7.92 (dd, J=7.7, 4.7 Hz, 1H), 7.59 (d, J=8.2 Hz, 1H), 7.45 (t, J=8.1 Hz, 1H), 7.23 (d, J=7.8 Hz, 1H), 2.76 (s, 3H). HRMS (ESI) m/z: 367.0501 [M+H]⁺, calcd for C$_{19}$H$_{12}$N$_2$O$_4$Cl 367.0480.

Example 14. Synthesis of Compound 18

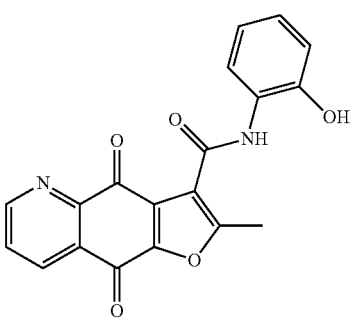

18

According to Preparation 3, using o-aminophenol as material to give the target yellow solid 18. $^1$H NMR (400 MHz, DMSO) δ 11.11 (s, 1H), 10.02 (s, 1H), 9.05 (d, J=3.3 Hz, 1H), 8.49 (d, J=6.7 Hz, 1H), 8.18 (d, J=7.8 Hz, 1H), 7.90 (dd, J=7.7, 4.7 Hz, 1H), 7.01-6.93 (m, 2H), 6.82 (t, J=7.3 Hz, 1H), 2.83 (s, 3H). HRMS (ESI) m/z: 347.0656 [M−H]⁻, calcd for C$_{19}$H$_{11}$N$_2$O$_5$ 347.0673.

Example 15. Synthesis of Compound 19

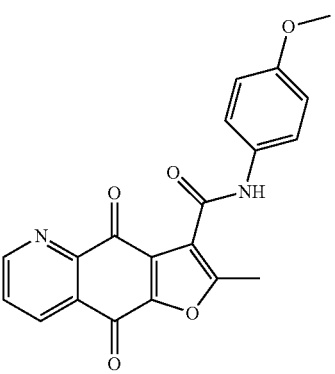

19

According to Preparation 3, using p-methoxyphenylamine as material to give the target red solid 19. $^1$H NMR (400 MHz, DMSO) δ 11.00 (s, 1H), 9.07 (d, J=3.3 Hz, 1H), 8.50 (dd, J=7.8, 1.6 Hz, 1H), 7.91 (dd, J=7.7, 4.7 Hz, 1H), 7.67 (d, J=9.0 Hz, 2H), 6.99 (d, J=9.0 Hz, 2H), 3.77 (s, 3H), 2.77 (s, 3H). HRMS (ESI) m/z: 361.0817 [M−H]⁻, calcd for C$_{20}$H$_{13}$N$_2$O$_5$ 361.0830.

Example 16. Synthesis of Compound 20

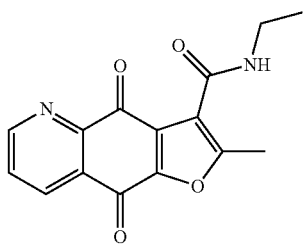

20

According to Preparation 3, using ethylamine as material to give the target yellow solid 20. $^1$H NMR (400 MHz, CDCl$_3$) δ 9.52 (s, 1H), 9.08 (d, J=3.3 Hz, 1H), 8.56 (d, J=7.4 Hz, 1H), 7.76 (dd, J=7.7, 4.7 Hz, 1H), 3.50 (q, J=6.5 Hz, 2H), 2.93 (s, 3H), 1.34 (t, J=7.2 Hz, 3H). HRMS (ESI) m/z: 307.0699 [M+Na]$^+$, calcd for C$_{15}$H$_{12}$N$_2$O$_4$Na 307.0689.

Example 17. Synthesis of Compound 22

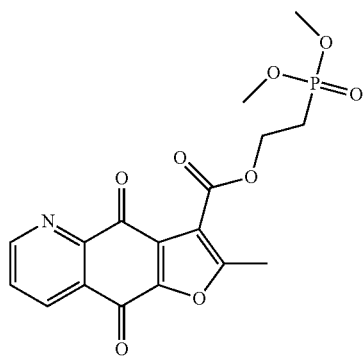

22

According to Preparation 3, using dimethyl 2-hydroxyethylphosphonate as material to give the target yellow solid 22. $^1$H NMR (400 MHz, CDCl$_3$) δ 9.06 (dd, J=4.6, 1.6 Hz, 1H), 8.54 (dd, J=7.9, 1.6 Hz, 1H), 7.71 (dd, J=7.9, 4.7 Hz, 1H), 4.64-4.58 (m, 2H), 3.80 (s, 3H), 3.77 (s, 3H), 2.77 (s, 3H), 2.54-2.39 (m, 2H). HRMS (ESI) m/z: 392.0538 [M−H]$^−$, calcd for C$_{17}$H$_{15}$NO$_8$P 392.0541.

Example 18. Synthesis of Compound 23

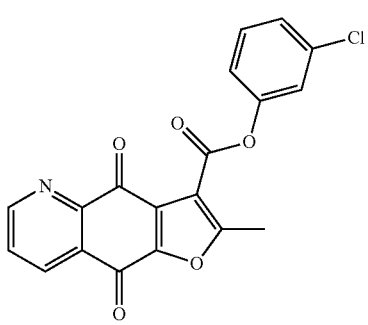

23

According to Preparation 3, using m-chlorophenol as material to give the target yellow solid 23. $^1$H NMR (400 MHz, CDCl$_3$) δ 9.07 (dd, J=4.6, 1.6 Hz, 1H), 8.56 (dd, J=7.9, 1.6 Hz, 1H), 7.72 (dd, J=7.9, 4.7 Hz, 1H), 7.52 (s, 1H), 7.39-7.35 (m, 2H), 7.30-7.26 (m, 1H), 2.83 (s, 1H). HRMS (ESI) m/z: 368.0341 [M+H]$^+$, calcd for C$_{19}$H$_{11}$NO$_5$Cl 368.0320.

Example 19. Synthesis of Compound 24

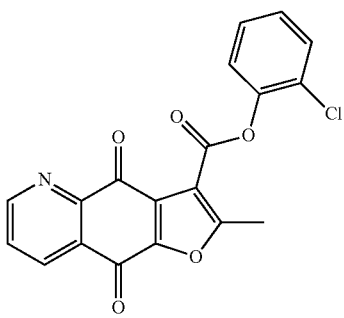

24

According to Preparation 3, using o-chlorophenol as material to give the target yellow solid 24. $^1$H NMR (400 MHz, CDCl$_3$) δ 9.06 (dd, J=4.6, 1.6 Hz, 1H), 8.56 (dd, J=7.9, 1.7 Hz, 1H), 7.72 (dd, J=7.9, 4.7 Hz, 1H), 7.53-7.49 (m, 2H), 7.38 (td, J=7.8, 1.5 Hz, 1H), 7.29-7.25 (m, 1H), 2.85 (s, 3H). HRMS (ESI) m/z: 368.0335 [M+H]$^+$, calcd for C$_{19}$H$_{10}$NO$_5$Cl 368.0320.

Example 20. Synthesis of Compound 25

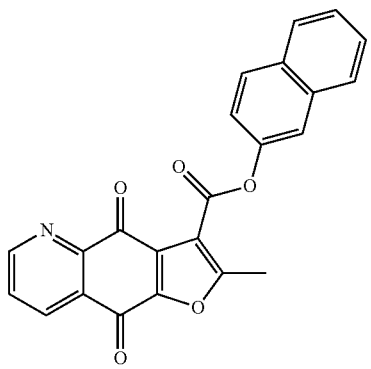

25

According to Preparation 3, using 2-naphthalenol as material to give the target yellow solid 25. $^1$H NMR (400 MHz, CDCl$_3$) δ 9.07 (d, J=4.6 Hz, 1H), 8.56 (d, J=7.8 Hz, 1H), 7.94-9.86 (m, 4H), 7.72 (dd, J=7.9, 4.6 Hz, 1H), 7.60 (dd, J=8.8, 2.2 Hz, 1H), 7.55-7.41 (m, 2H), 2.86 (s, 3H). HRMS (ESI) m/z: 382.0706 [M−H]$^−$, calcd for C$_{23}$H$_{12}$NO$_5$ 382.0721.

Example 21. Synthesis of Compound 26

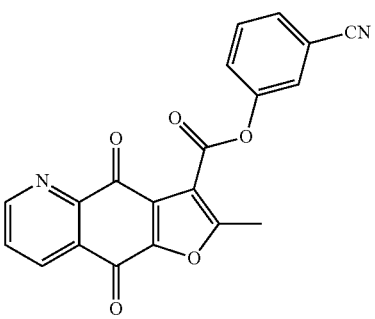

26

According to Preparation 3, using 3-hydroxybenzonitrile as material to give the target yellow solid 26. $^1$H NMR (400 MHz, CDCl$_3$) δ 9.08 (dd, J=4.7, 1.7 Hz, 1H), 8.57 (dd, J=7.9, 1.7 Hz, 1H), 7.82 (s, 1H), 7.79-7.75 (m, 1H), 7.74 (dd, J=7.9, 4.7 Hz, 1H), 7.66-7.48 (m, 2H), 2.84 (s, 3H). HRMS (ESI) m/z: 359.0679 [M+H]$^+$, calcd for C$_{20}$H$_{11}$N$_2$O$_5$ 359.0662.

Example 22. Synthesis of Compound 27

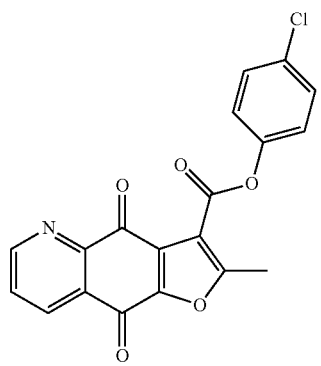

According to Preparation 3, using p-chlorophenol as material to give the target yellow solid 27. $^1$H NMR (400 MHz, CDCl$_3$) δ 9.07 (dd, J=4.6, 1.6 Hz, 1H), 8.56 (dd, J=7.9, 1.6 Hz, 1H), 7.72 (dd, J=7.9, 4.7 Hz, 1H), 7.41 (br, s, 4H), 2.82 (s, 3H). HRMS (ESI) m/z: 368.0334 [M+H]$^+$, calcd for C$_{19}$H$_{11}$NO$_5$Cl 368.0320.

Example 23. Synthesis of Compound 28

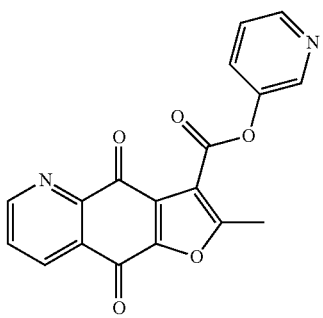

According to Preparation 3, using 3-hydroxyl pyridine as material to give the target yellow solid 28. $^1$H NMR (400 MHz, CDCl$_3$) δ 9.08 (dd, J=4.7, 1.7 Hz, 1H), 8.77 (d, J=2.5 Hz, 1H), 8.58-8.55 (m, 2H), 7.87 (ddd, J=8.3, 2.7, 1.4 Hz, 1H), 7.73 (dd, J=7.9, 4.7 Hz, 1H), 7.43 (dd, J=8.3, 4.8 Hz, 1H), 2.85 (s, 3H). HRMS (ESI) m/z: 335.0673 [M+H]$^+$, calcd for C$_{18}$H$_{11}$N$_2$O$_5$ 335.0662.

Example 24. Synthesis of Compound 31

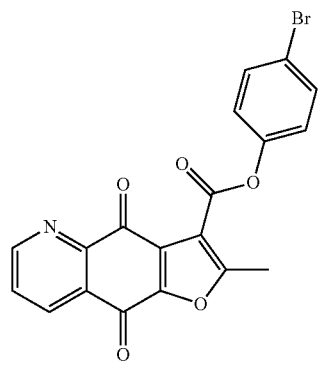

According to Preparation 3, using 4-bromophenol as material to give the target yellow solid 31. $^1$H NMR (400 MHz, CDCl$_3$) δ 9.07 (dd, J=4.7, 1.7 Hz, 1H), 8.56 (dd, J=7.9, 1.7 Hz, 1H), 7.72 (dd, J=7.9, 4.7 Hz, 1H), 7.56 (d, J=8.8 Hz, 2H), 7.36 (d, J=8.8 Hz, 2H), 2.82 (s, 3H). HRMS (ESI) m/z: 411.9820 and 413.9865 [M+H]$^+$, calcd for C$_{19}$H$_{11}$NO$_5$Br 411.9815 and 413.9797.

Example 25. Synthesis of Compound 32

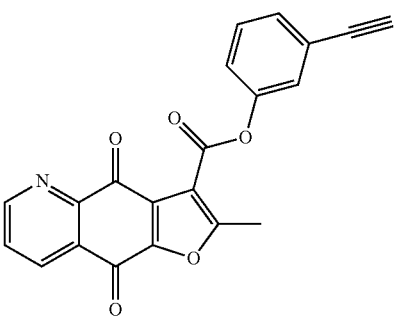

According to Preparation 3, using 3-ethynylphenol as material to give the target yellow solid 32. $^1$H NMR (400 MHz, CDCl$_3$) δ 9.07 (dd, J=4.6, 1.5 Hz, 1H), 8.56 (dd, J=7.9, 1.7 Hz, 1H), 7.72 (dd, J=7.9, 4.7 Hz, 1H), 7.60 (s, 1H), 7.50-7.34 (m, 3H), 3.12 (s, 1H), 2.83 (s, 3H). HRMS (ESI) m/z: 380.0543 [M+Na]$^+$, calcd for C$_{21}$H$_{11}$NO$_5$Na 380.0529.

Example 26. Synthesis of Compound 35

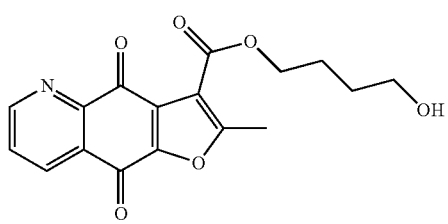

According to Preparation 3, using butane-1,4-diol as material to give the target yellow solid 35. ¹H NMR (400 MHz, CDCl3) δ 9.06 (d, J=3.5 Hz, 1H), 8.54 (dd, J=7.8, 1.1 Hz, 1H), 7.71 (dd, J=7.8, 4.6 Hz, 1H), 4.43 (t, J=6.4 Hz, 2H), 3.75 (t, J=6.3 Hz, 2H), 2.76 (s, 3H), 2.00-1.92 (m, 2H), 1.85-1.78 (m, 2H). HRMS (ESI) m/z: 352.0810 [M+Na]⁺, calcd for $C_{17}H_{15}NO_6Na$ 352.0792.

Example 27. Synthesis of Compound 36

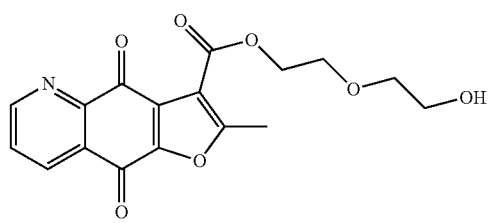

According to Preparation 3, using 2,2'-oxydiethanol as material to give the target yellow solid 36. ¹H NMR (400 MHz, CDCl₃) δ 9.05 (dd, J=4.7, 1.7 Hz, 1H), 8.53 (dd, J=7.9, 1.7 Hz, 1H), 7.71 (dd, J=7.9, 4.7 Hz, 1H), 4.54 (t, J=4.6 Hz, 2H), 3.93 (t, J=4.8 Hz, 2H), 3.79 (t, J=4.4 Hz, 2H), 3.70 (t, J=4.4 Hz, 2H), 2.76 (s, 3H). HRMS (ESI) m/z: 368.0752 [M+Na]⁺, calcd for $C_{17}H_{15}NO_7Na$ 368.0741.

Example 28. Synthesis of Compound 37

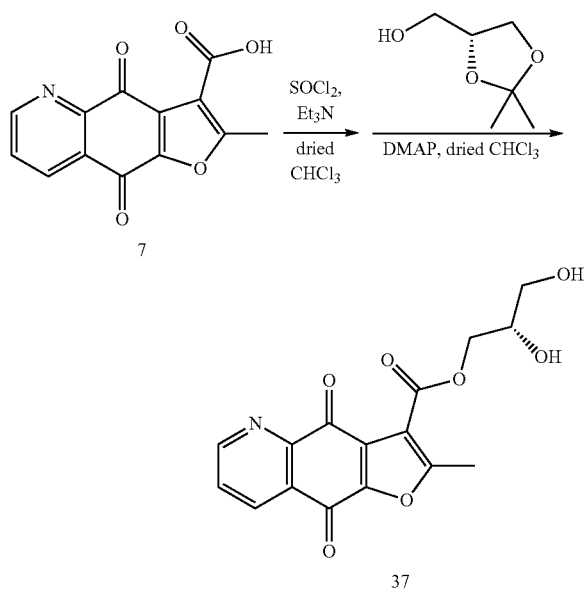

According to Preparation 3, using (R)-(2,2-dimethyl-1,3-dioxolan-4-yl)methanol as material to give the target yellow solid 37. ¹H NMR (400 MHz, CDCl₃) δ 9.09 (dd, J=4.6, 1.6 Hz, 1H), 8.57 (dd, J=7.8, 1.5 Hz, 1H), 7.75 (dd, J=7.8, 4.7 Hz, 1H), 4.48 (d, J=4.7 Hz, 2H), 4.19 (m, 1H), 3.85-3.76 (m, 2H), 2.81 (s, 3H).

Example 29. Synthesis of Compounds 38 and 45

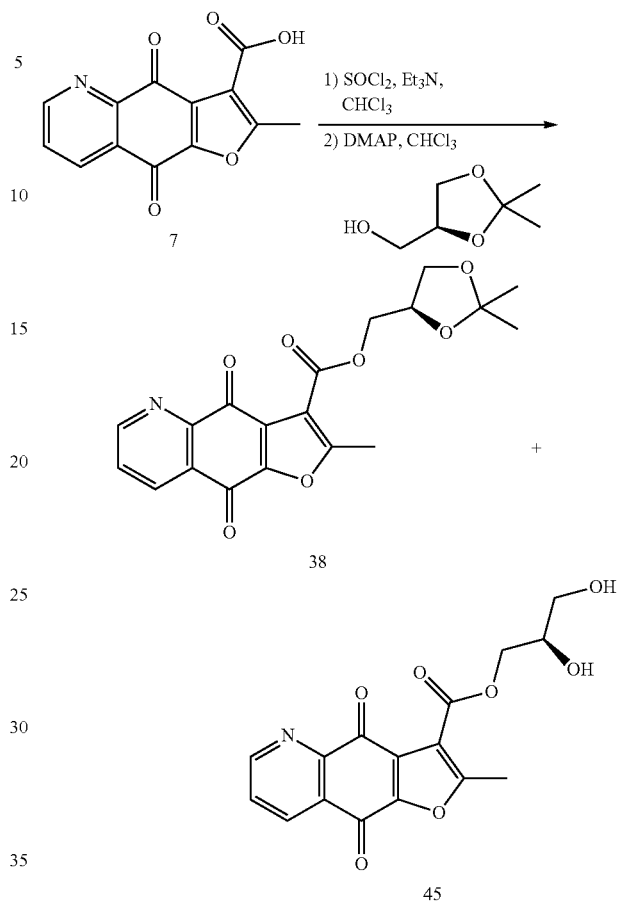

According to Preparation 3, using (S)-(2,2-dimethyl-1,3-dioxolan-4-yl)methanol as material to give two yellow solids, 38 and 45.
38: ¹H NMR (400 MHz, CDCl₃) δ 8.99 (dd, J=4.7, 1.7 Hz, 1H), 8.47 (dd, J=7.9, 1.7 Hz, 1H), 7.64 (dd, J=7.9, 4.7 Hz, 1H), 4.54-4.46 (m, 1H), 4.36 (dd, J=11.0, 5.4 Hz, 1H), 4.30 (dd, J=11.0, 6.5 Hz, 1H), 4.19 (dd, J=8.7, 6.3 Hz, 1H), 3.94 (dd, J=8.7, 5.4 Hz, 1H), 2.70 (s, 3H), 1.37 (s, 3H), 1.31 (s, 3H). HRMS (ESI) m/z: 394.0909 [M+Na]⁺, calcd for $C_{19}H_{17}NO_7Na$ 394.0897.
45: ¹H NMR (400 MHz, CDCl₃) δ 9.01 (dd, J=4.7, 1.7 Hz, 1H), 8.48 (dd, J=7.9, 1.7 Hz, 1H), 7.66 (dd, J=7.9, 4.7 Hz, 1H), 4.40 (d, J=5.2 Hz, 2H), 4.14-4.08 (m, 1H), 3.76-3.63 (m, 2H), 2.73 (s, 3H). HRMS (ESI) m/z: 354.0596 [M+Na]⁺, calcd for $C_{16}H_{13}NO_7Na$ 354.0584.

Example 30. Synthesis of Compound 39

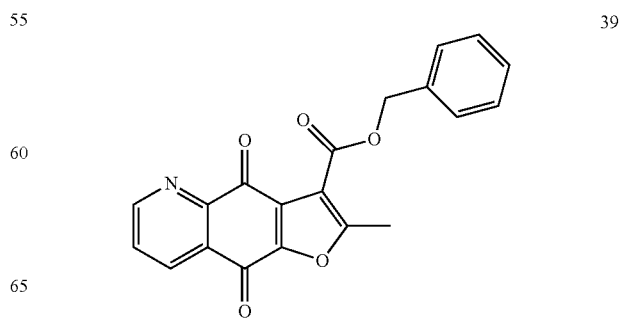

According to Preparation 3, using phenylmethanol as material to give the target yellow solid 39. $^1$H NMR (400 MHz, CDCl3) δ 9.06 (dd, J=4.6, 1.6 Hz, 1H), 8.53 (dd, J=7.9, 1.6 Hz, 1H), 7.69 (dd, J=7.8, 4.7 Hz, 1H), 7.58-7.56 (m, 2H), 7.42-7.37 (m, 2H), 7.35-7.31 (m, 1H), 5.42 (s, 2H), 2.73 (s, 3H). HRMS (ESI) m/z: 370.0704 [M+Na]$^+$, calcd for C$_{20}$H$_{13}$NO$_5$Na 370.0686.

Example 31. Synthesis of Compound 40

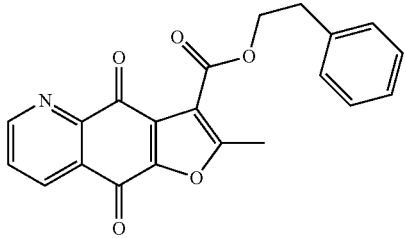

According to Preparation 3, using 2-phenylethanol as material to give the target yellow solid 40. $^1$H NMR (400 MHz, CDCl3) δ 9.07 (dd, J=4.7, 1.7 Hz, 1H), 8.54 (dd, J=7.9, 1.7 Hz, 1H), 7.70 (dd, J=7.9, 4.7 Hz, 1H), 7.33-7.28 (m, 4H), 7.25-7.20 (m, 1H), 4.60 (t, J=7.3 Hz, 2H), 3.19 (t, J=7.3 Hz, 2H), 2.65 (s, 3H). HRMS (ESI) m/z: 384.0864 [M+Na]$^+$, calcd for C$_{21}$H$_{15}$NO$_5$Na 384.0842.

Example 32. Synthesis of Compound 58

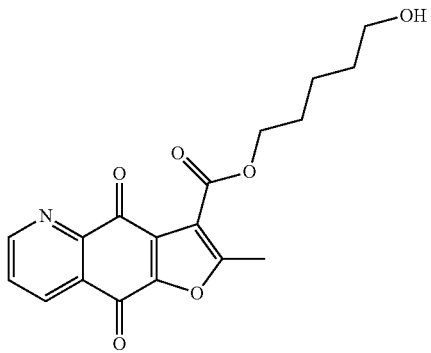

According to Preparation 3, using pentane-1,5-diol as material to give the target yellow solid 45. $^1$H NMR (400 MHz, CDCl$_3$) δ 9.05 (dd, J=4.7, 1.7 Hz, 1H), 8.53 (dd, J=7.9, 1.7 Hz, 1H), 7.70 (dd, J=7.9, 4.7 Hz, 1H), 4.40 (t, J=6.5 Hz, 2H), 3.71 (t, J=6.1 Hz, 2H), 2.76 (s, 3H), 1.93-1.85 (m, 2H), 1.73-1.55 (m, 4H). HRMS (ESI) m/z: 366.0966 [M+Na]$^+$, calcd for C$_{18}$H$_{17}$NO$_6$Na 366.0948.

Example 33. Synthesis of Compound 46

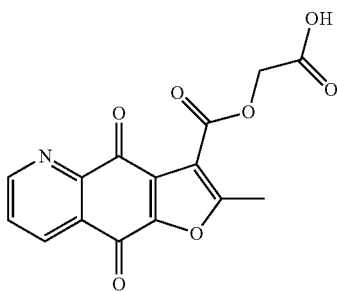

According to Preparation 3, using 2-hydroxyl acetic acid as material to give the target yellow solid 46. $^1$H NMR (400 MHz, MeOD) δ 8.95 (dd, J=4.7, 1.6 Hz, 1H), 8.58 (dd, J=7.9, 1.6 Hz, 1H), 7.84 (dd, J=7.9, 4.8 Hz, 1H), 4.07 (s, 2H), 2.78 (s, 3H). HRMS (ESI) m/z: 338.0283 [M+Na]$^+$, calcd for C$_{15}$H$_9$NO$_7$Na 338.0271.

Example 34. Synthesis of Compound 47

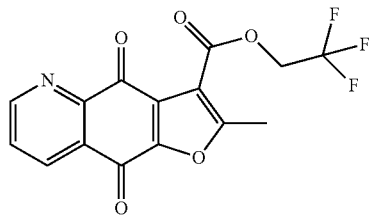

According to Preparation 3, using trifloroethanol as material to give the target yellow solid 47. $^1$H NMR (400 MHz, CDCl$_3$) δ 9.07 (dd, J=4.7, 1.7 Hz, 1H), 8.54 (dd, J=7.9, 1.7 Hz, 1H), 7.71 (dd, J=7.9, 4.7 Hz, 1H), 4.77 (q, J=8.3 Hz, 2H), 2.78 (s, 3H). HRMS (ESI) m/z: 362.0266 [M+Na]$^+$, calcd for C$_{15}$H$_8$NO$_5$F$_3$Na 362.0247.

Example 35. Synthesis of Compound 48

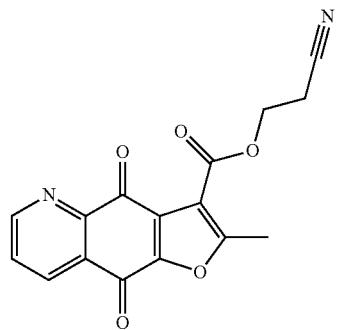

According to Preparation 3, using 3-hydroxypropanenitrile as material to give the target yellow solid 48. $^1$H NMR (400 MHz, CDCl$_3$) δ 9.06 (dd, J=4.6, 1.6 Hz, 1H), 8.54 (dd, J=7.9, 1.7 Hz, 1H), 7.72 (dd, J=7.9, 4.7 Hz, 1H), 4.60 (t, J=6.5 Hz, 2H), 2.99 (t, J=6.5 Hz, 2H), 2.78 (s, 3H).

Example 36. Synthesis of Compound 49

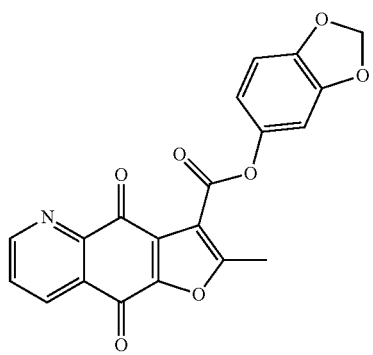

According to Preparation 3, using benzo[d][1,3]dioxol-5-ol as material to give the target yellow solid 49. $^1$H NMR (400 MHz, CDCl$_3$) δ 9.06 (dd, J=4.7, 1.7 Hz, 1H), 8.55 (dd, J=7.9, 1.7 Hz, 1H), 7.72 (dd, J=7.9, 4.7 Hz, 1H), 6.97 (d, J=2.3 Hz, 1H), 6.89 (dd, J=8.4, 2.3 Hz, 1H), 6.82 (d, J=8.4 Hz, 1H), 6.01 (s, 2H), 2.81 (s, 2H).

Example 37. Synthesis of Compound 43

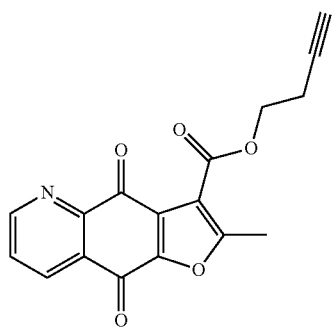

According to Preparation 3, using prop-2-yn-1-ol as material to give the target yellow solid 43. $^1$H NMR (400 MHz, CDCl$_3$) δ 9.06 (d, J=4.5 Hz, 1H), 8.54 (d, J=7.7 Hz, 1H), 7.70 (dd, J=7.8, 4.6 Hz, 1H), 4.50 (t, J=7.0 Hz, 2H), 2.88-2.64 (m, 5H), 2.02 (t, J=2.6 Hz, 1H). HRMS (ESI) m/z: 332.0544 [M+Na]$^+$, calcd for C$_{17}$H$_{11}$NO$_5$Na 332.0529.

Example 38. Synthesis of Compound 44

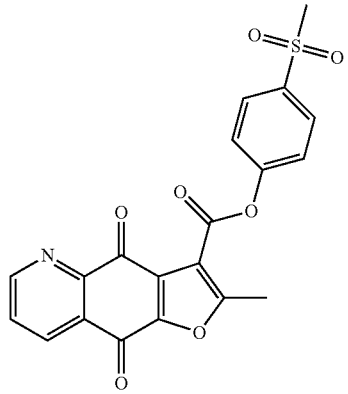

According to Preparation 3, using 4-(methylsulfonyl)phenol as material to give the target yellow solid 44. $^1$H NMR (400 MHz, CDCl$_3$) δ 9.10 (dd, J=4.7, 1.7 Hz, 1H), 8.59 (dd, J=7.9, 1.7 Hz, 1H), 8.11-8.03 (m, 2H), 7.76 (dd, J=7.9, 4.7 Hz, 1H), 7.76-7.63 (m, 2H), 3.11 (s, 3H), 2.86 (s, 3H). HRMS (ESI) m/z: 434.0334 [M+H]$^+$, calcd for C$_{20}$H$_{13}$NO$_7$SNa 434.0305.

Example 39. Synthesis of Compound 50

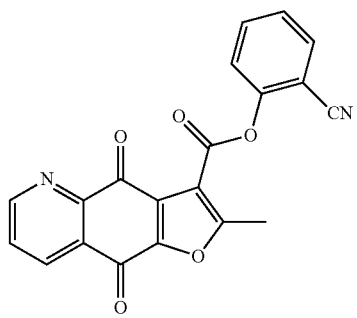

According to Preparation 3, using 2-hydroxybenzonitrile as material to give the target yellow solid 50. $^1$H NMR (400 MHz, CDCl$_3$) δ 9.06 (dd, J=4.7, 1.7 Hz, 1H), 8.57 (dd, J=7.9, 1.7 Hz, 1H), 7.92-7.61 (m, 4H), 7.42 (td, J=7.5, 1.4 Hz, 1H), 2.87 (s, 3H). HRMS (ESI) m/z: 381.0503 [M+Na]$^+$, calcd for C$_{20}$H$_{10}$N$_2$O$_5$Na 381.0482.

Example 40. Synthesis of Compound 51

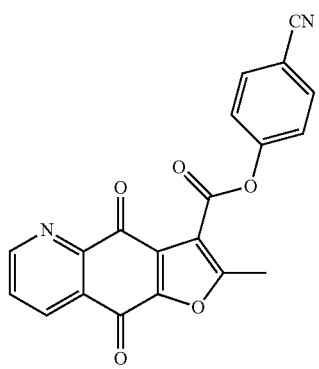

According to Preparation 3, using 4-hydroxybenzonitrile as material to give the target yellow solid 51. $^1$H NMR (400 MHz, CDCl$_3$) δ 9.08 (dd, J=4.7, 1.7 Hz, 1H), 8.57 (dd, J=7.9, 1.7 Hz, 1H), 7.76 (d, J=8.8 Hz, 1H), 7.74 (dd, J=7.0, 3.7 Hz, 2H), 7.63 (d, J=8.8 Hz, 2H), 2.84 (s, 3H). HRMS (ESI) m/z: 381.0496 [M+Na]$^+$, calcd for C$_{20}$H$_{10}$N$_2$O$_5$Na 381.0482.

Example 41. Synthesis of Compound 52

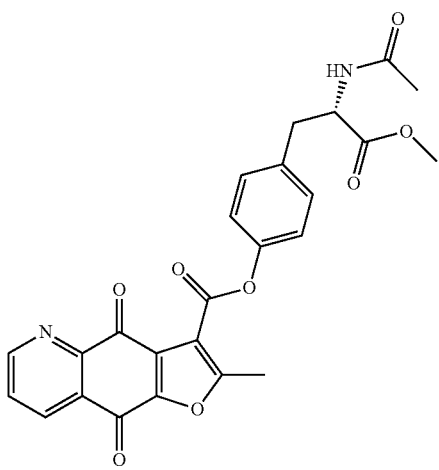

According to Preparation 3, using N-acetyl-L-tyrosine methyl ester as material to give the target yellow solid 52. $^1$H NMR (400 MHz, CDCl$_3$) δ 9.06 (dd, J=4.7, 1.7 Hz, 1H), 8.56 (dd, J=7.9, 1.7 Hz, 1H), 7.72 (dd, J=7.9, 4.7 Hz, 1H), 7.38 (d, J=8.5 Hz, 2H), 7.17 (d, J=8.5 Hz, 2H), 5.98 (d, J=7.5 Hz, 1H), 4.91 (dt, J=7.7, 5.7 Hz, 1H), 3.75 (s, 3H), 3.17 (dd, J=5.6, 3.4 Hz, 2H), 2.82 (s, 3H), 2.02 (s, 3H). ESI/MS m/z: 477.1 [M+H]$^+$.

Example 42. Synthesis of Compounds 53 and 54

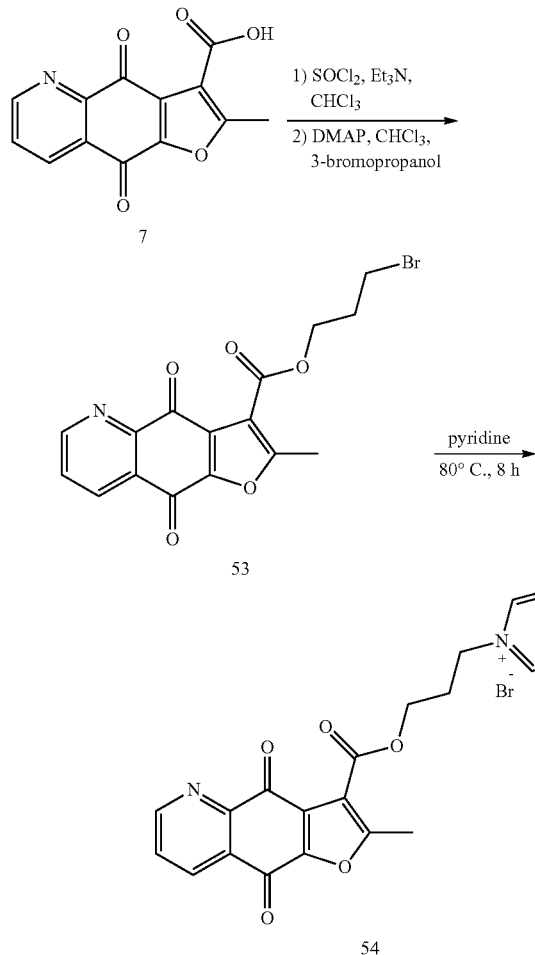

According to Preparation 3, using 3-bromopropanol as material to give the target yellow solid 53. $^1$H NMR (400 MHz, CDCl$_3$) δ 9.06 (dd, J=4.7, 1.7 Hz, 1H), 8.54 (dd, J=7.9, 1.7 Hz, 1H), 7.70 (dd, J=7.9, 4.7 Hz, 1H), 4.54 (t, J=5.8 Hz, 2H), 3.75 (t, J=5.4 Hz, 2H), 2.78 (s, 3H), 2.45-2.36 (m, 2H). HRMS (ESI) m/z: 377.9996 and 380.0005 [M+H]$^+$, calcd for C$_{16}$H$_{12}$NO$_5$Br 377.9972 and 379.9953.

The solution of 53 (20 mg, 0.05 mmol) in pyridine (5 ml) was heated under 80 for 8 h. And then, the reaction solution was cooled to room temperature, and added with ether (5 ml). The precipitate was filtered, and washed with ether (10 ml) and ethyl acetate (5 ml), respectively, to give the target yellow solid 54. $^1$H NMR (400 MHz, MeOD) δ 9.20 (d, J=5.6 Hz, 2H), 9.02 (dd, J=4.7, 1.6 Hz, 1H), 8.64-8.60 (m, 2H), 8.18 (t, J=7.2 Hz, 2H), 7.89 (dd, J=7.9, 4.8 Hz, 1H), 5.08 (t, J=7.4 Hz, 2H), 4.46 (t, J=5.6 Hz, 2H), 2.74 (s, 3H), 2.64-2.48 (m, 2H). HRMS (ESI) m/z: 377.1149 [M−Br]$^+$, calcd for C$_{21}$H$_{17}$N$_2$O$_5$ 377.1132.

Example 43. Synthesis of Compound 55

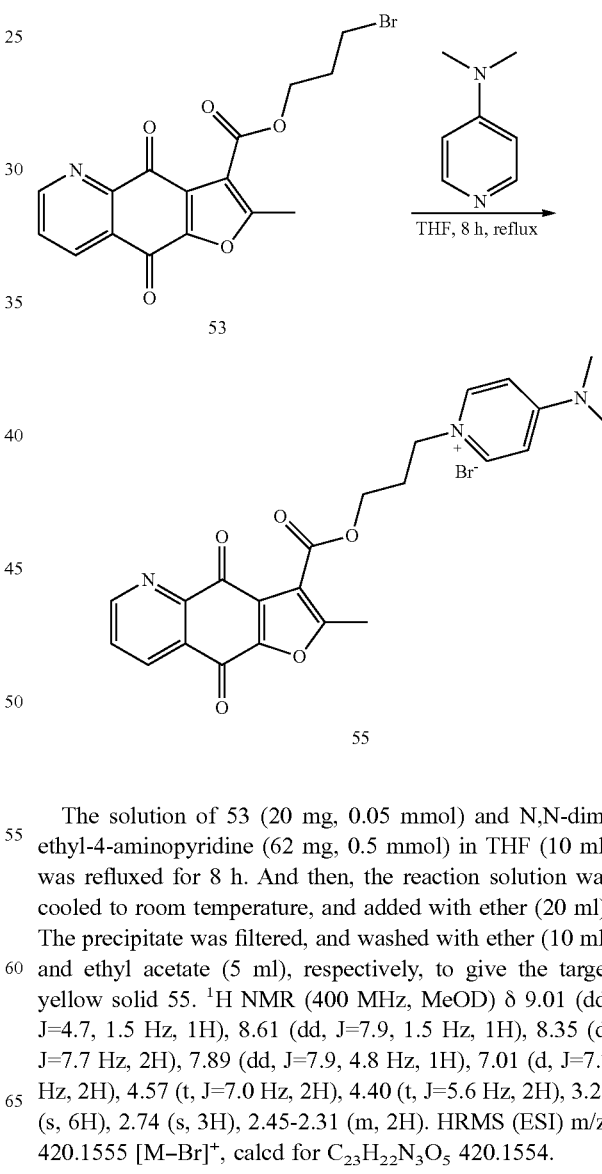

The solution of 53 (20 mg, 0.05 mmol) and N,N-dimethyl-4-aminopyridine (62 mg, 0.5 mmol) in THF (10 ml) was refluxed for 8 h. And then, the reaction solution was cooled to room temperature, and added with ether (20 ml). The precipitate was filtered, and washed with ether (10 ml) and ethyl acetate (5 ml), respectively, to give the target yellow solid 55. $^1$H NMR (400 MHz, MeOD) δ 9.01 (dd, J=4.7, 1.5 Hz, 1H), 8.61 (dd, J=7.9, 1.5 Hz, 1H), 8.35 (d, J=7.7 Hz, 2H), 7.89 (dd, J=7.9, 4.8 Hz, 1H), 7.01 (d, J=7.7 Hz, 2H), 4.57 (t, J=7.0 Hz, 2H), 4.40 (t, J=5.6 Hz, 2H), 3.21 (s, 6H), 2.74 (s, 3H), 2.45-2.31 (m, 2H). HRMS (ESI) m/z: 420.1555 [M−Br]$^+$, calcd for C$_{23}$H$_{22}$N$_3$O$_5$ 420.1554.

Example 44. Preparation 4: Synthesis of Compound 33

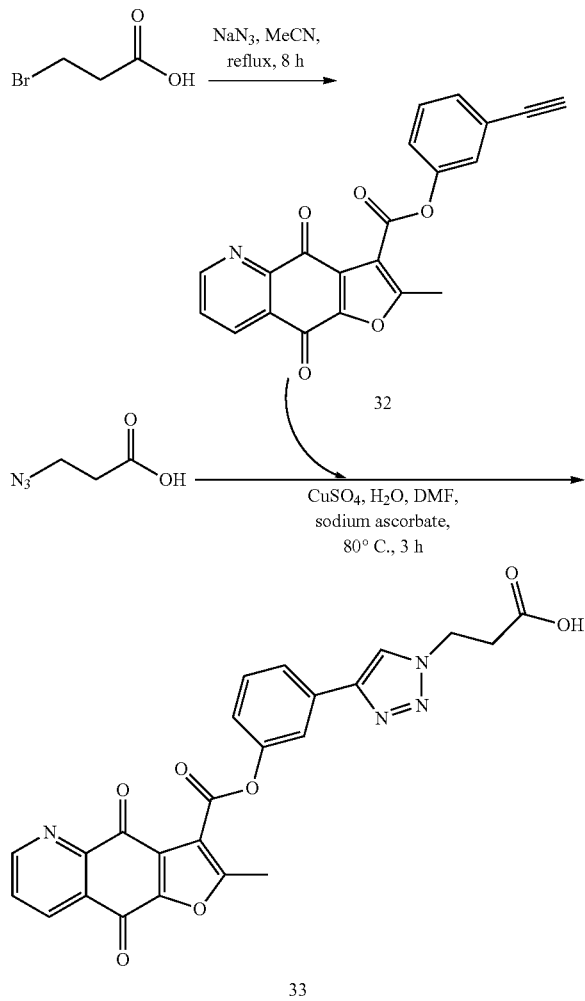

Example 45. Synthesis of Compound 34

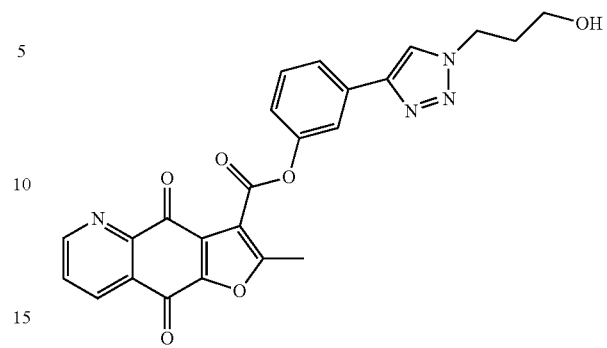

According to Preparation 4, using 3-bromopropanol as material to give the target yellow solid 34. $^1$H NMR (400 MHz, CDCl$_3$) δ 9.08 (dd, J=4.7, 1.7 Hz, 1H), 8.58 (dd, J=7.9, 1.7 Hz, 1H), 7.93 (s, 1H), 7.85-7.82 (m, 2H), 7.74 (dd, J=7.9, 4.7 Hz, 1H), 7.52 (t, J=7.9 Hz, 1H), 7.44-7.37 (m, 1H), 4.61 (t, J=6.7 Hz, 2H), 3.72 (t, J=5.8 Hz, 2H), 2.85 (s, 3H), 2.21 (quint, J=6.2 Hz, 2H). HRMS (ESI) m/z: 457.1138 [M–H]$^-$, calcd for C$_{24}$H$_{17}$N$_4$O$_6$ 457.1154.

Example 46. Synthesis of Compound 42

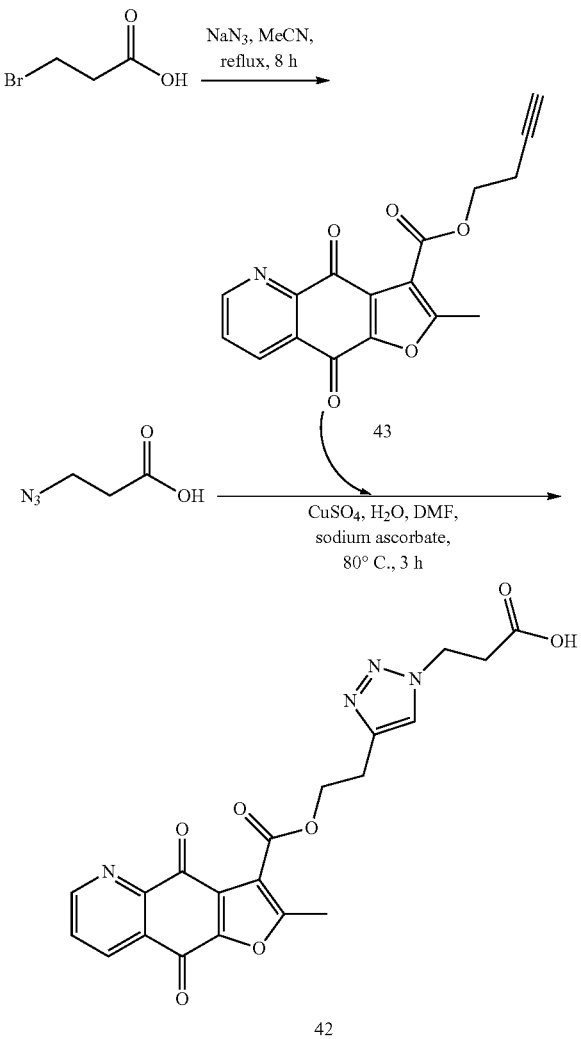

To the solution of 3-bromopropanoic acid (152 mg, 1 mmol) in MeCN (20 ml), NaN$_3$ (130 mg, 2 mmol) was added. The solution was refluxed for 8 h. The reaction solution was concentrated under reduced pressure to give white solid. The resultant white solid was dissolved in water (5 ml), and was added with compound 32 (60 mg, 0.17 mmol), CuSO$_4$ (3 mg), sodium ascorbate (2.5 mg) and DMF (5 ml), respectively. The solution was heated to 80° C. for 3 h. And then, the reaction solution was cooled to room temperature, and added with water (50 ml). The resultant suspension was extracted with CH$_2$Cl$_2$ (20 ml×2). The combined organic solution was washed with water (10 ml×3) and saturated saline solution (10 ml×2). The organic solution was concentrated under reduced pressure and purified by silica gel column chromatography to give the target yellow solid 33. $^1$H NMR (400 MHz, DMSO) δ 12.54 (s, 1H), 9.04 (dd, J=4.6, 1.6 Hz, 1H), 8.68 (s, 1H), 8.50 (dd, J=7.9, 1.6 Hz, 1H), 7.89 (dd, J=7.9, 4.7 Hz, 1H), 7.85 (d, J=1.9 Hz, 1H), 7.82 (d, J=7.8 Hz, 1H), 7.60 (t, J=7.9 Hz, 1H), 7.35 (dd, J=8.1, 1.4 Hz, 1H), 4.63 (t, J=6.7 Hz, 2H), 2.97 (t, J=6.7 Hz, 2H), 2.81 (s, 3H). HRMS (ESI) m/z: 471.0920 [M–H]$^-$, calcd for C$_{24}$H$_{15}$N$_4$O$_7$ 471.0946.

According to Preparation 4, using compound 43 as material to give the target yellow solid 42. $^1$H NMR (400 MHz, CDCl$_3$) δ 8.99 (dd, J=4.8, 1.4 Hz, 1H), 8.65 (dd, J=7.9, 1.5 Hz, 1H), 8.19 (s, 1H), 7.83 (dd, J=7.9, 4.8 Hz, 1H), 4.78 (t, J=5.6 Hz, 2H), 4.70 (t, J=5.0 Hz, 2H), 3.24 (t, J=5.0 Hz, 2H), 2.92 (t, J=5.6 Hz, 2H), 2.79 (s, 2H). HRMS (ESI) m/z: 423.0923 [M−H]$^−$, calcd for C$_{20}$H$_{15}$N$_4$O$_7$ 423.0946.

Example 47. Synthesis of Compound 56

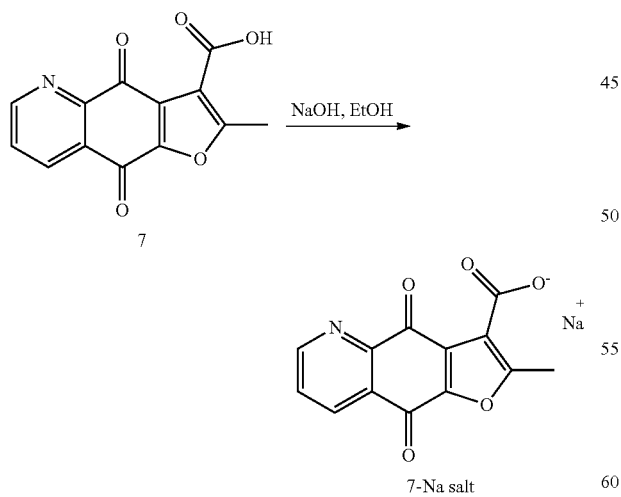

According to Synthesis of 42, using 3-bromopropanol as material to give the target yellow solid 56. $^1$H NMR (400 MHz, CDCl$_3$) δ 9.02 (d, J=4.5 Hz, 1H), 8.57 (dd, J=7.9, 1.6 Hz, 1H), 7.98 (s, 1H), 7.75 (dd, J=7.9, 4.7 Hz, 1H), 4.70 (t, J=5.6 Hz, 2H), 4.58 (t, J=5.6 Hz, 2H), 3.68 (t, J=5.8 Hz, 2H), 3.27 (t, J=5.6 Hz, 2H), 2.76 (s, 3H), 2.15 (quint, J=6 Hz, 2H). HRMS (ESI) m/z: 433.1142 [M+Na]$^+$, calcd for C$_{20}$H$_{18}$N$_4$O$_6$Na 433.1119.

Example 48. Synthesis of Compound 7-Na Salt

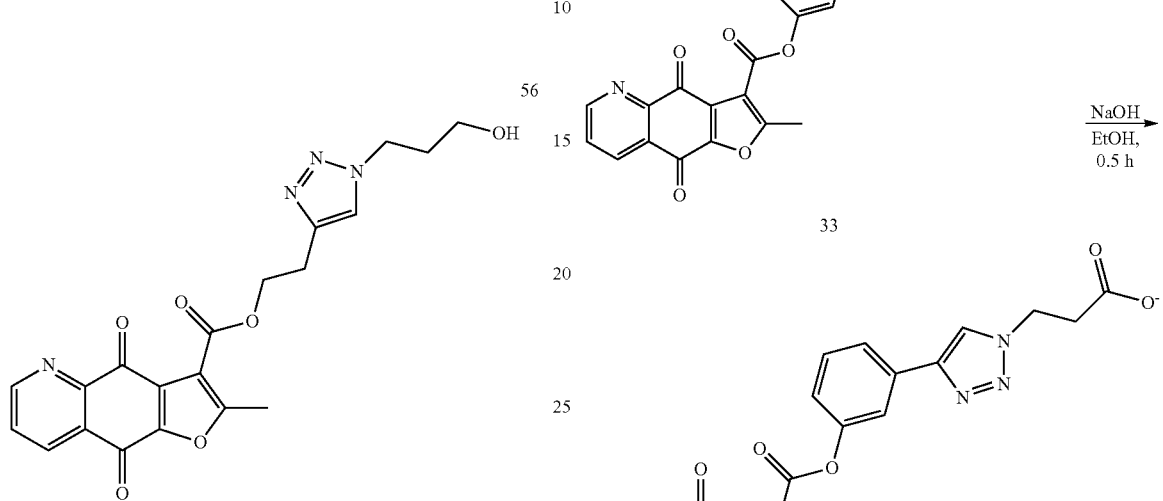

To a solution of 7 (52 mg, 0.20 mmol) in ethanol (10 ml), a solution of NaOH (8 mg, 0.2 mmol) in ethanol (5 ml) was added dropwish. The solution was stirred at room temperature for 30 min. The precipitate was filtered, washed with ethanol (1 ml×2) and dried to give the target yellow solid 7-Na salt.

Example 49. Synthesis of Compound 33-Na Salt

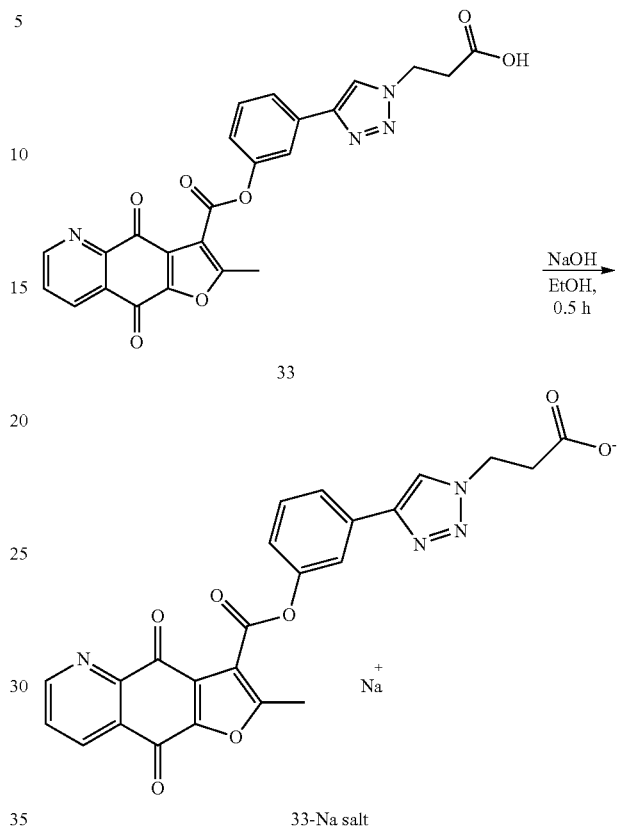

According to Synthesis of 7-Na salt, using compound 33 as material to give the target yellow solid 33-Na salt.

Example 50. Synthesis of Compound 57

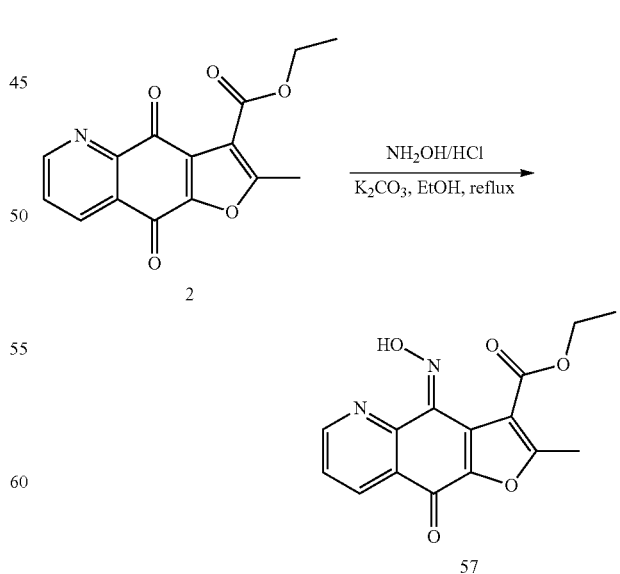

The solution of 2 (72 mg, 0.25 mmol), hydroxylamine hydrochloride (52 mg, 0.75 mmol) and K$_2$CO$_3$ (52 mg, 0.375 mmol) in ethanol (10 ml) was stirred and refluxed for 1.5 h. The reaction solution was concentration under reduced pressure. The resultant solid was purified by silica gel column chromatography to give the target yellow solid 57. $^1$H NMR (400 MHz, CDCl$_3$) δ 8.76-8.74 (m, 2H), 7.76 (dd, J=8.0, 5.0 Hz, 1H), 4.42 (q, J=7.1 Hz, 2H), 2.64 (s, 3H), 1.41 (t, J=7.1 Hz, 3H).

Example 51. Additional Compounds

The following compounds can be prepared by the methods shown in Examples 1-50. Routine changes in reagents and reaction conditions needed to make the particular compounds will be apparent to those of skill in the art.

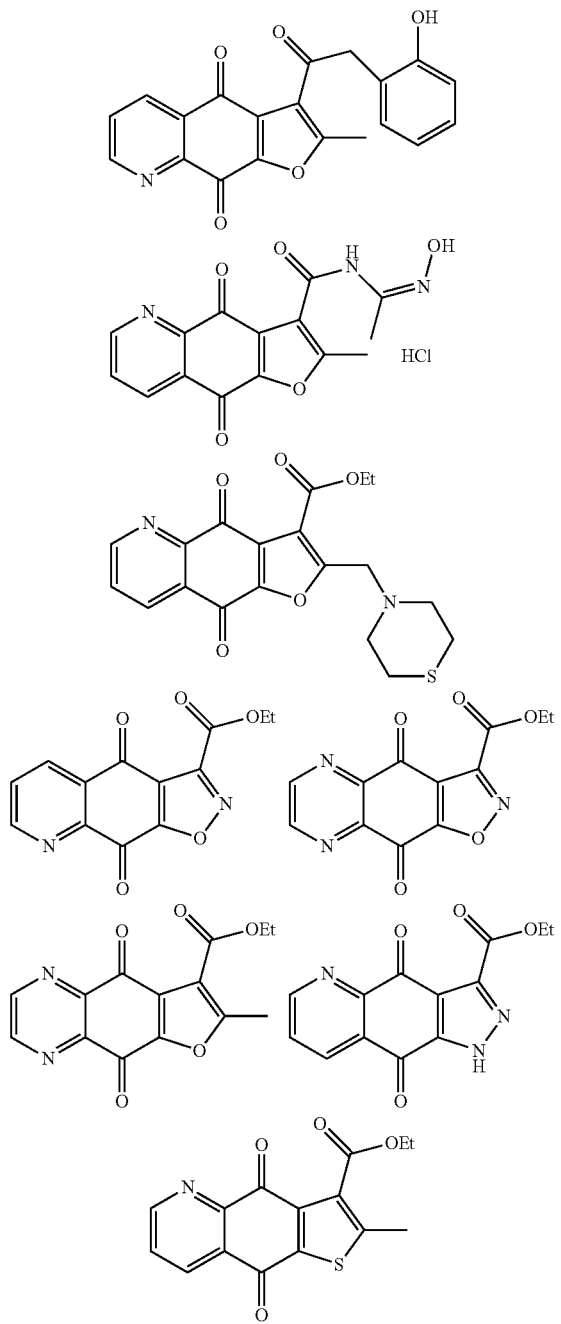
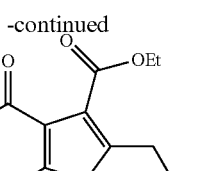
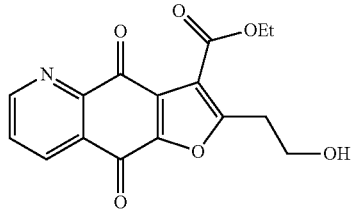

Example 52. Whole Cell Extract Tdp1 Assay

DT40 knockout cells (1×10$^7$) for Tdp1 (TDP1−/−) complemented with human TDP1 (hTDP1) were collected, washed, and centrifuged. Cell pellets were then resuspended in 100 μL of CellLytic M cell lysis reagent (SIGMA-Aldrich C2978). After 15 min on ice, lysates were centrifuged at 12,000 g for 10 min, and supernatants were transferred to a new tube. Protein concentrations were determined using a Nanodrop spectrophotometer (Invitrogen), and whole cell extracts were stored at −80° C. A 5'-[$^{32}$P]-labeled single-stranded DNA oligonucleotide containing a 3'-phosphotyrosine (N14Y) was incubated at 1 nM with 4 μg/mL of whole cell extracts in the absence or presence of inhibitor for 15 min at room temperature in the WCE buffer containing 50 mM Tris HCl, pH 7.5, 80 mM KCl, 2 mM EDTA, 1 mM DTT, 40 μg/mL BSA, and 0.01% Tween-20. Reactions were terminated by the addition of 1 volume of gel loading buffer [99.5% (v/v) formamide, 5 mM EDTA, 0.01% (w/v) xylene cyanol, and 0.01% (w/v) bromophenol blue]. Samples were subjected to a 16% denaturing PAGE with multiple loadings at 12-min intervals. Gels were dried and exposed to a PhosphorImager screen (GE Healthcare). Gel images were scanned using a Typhoon 8600 (GE Healthcare), and densitometry analyses were performed using the ImageQuant software (GE Healthcare).

Example 53. Recombinant TDP1 Assay

The N14Y DNA substrate was incubated at 1 nM with 10 pM recombinant TDP1 in the absence or presence of inhibitor for 15 min at room temperature in WCE buffer (see Example 51). When indicated, parallel reactions were performed in the HTS assay buffer containing 1×PBS, pH 7.4, 80 mM KCl, and 0.01% Tween-20. Samples were then analyzed similarly to the WCE TDP1 assay (Example 51).

Example 54. Recombinant TDP2 Assay

TDP2 reactions were carried out as described previously (Example 52) with the following modifications. The 18-mer single-stranded oligonucleotide DNA substrate (α$^{32}$P-cordycepin-3'-labeled) was incubated at 1 nM with 25 pM recombinant human TDP2 in the absence or presence of inhibitor for 15 min at room temperature in a buffer containing 50 mM Tris-HCl, pH 7.5, 80 mM KCl, 5 mM MgCl$_2$, 0.1 mM EDTA, 1 mM DTT, 40 μg/mL BSA, and 0.01% Tween 20. Reactions were terminated and treated similarly to WCE and recombinant TDP1 reactions (see Examples 52 and 53).

Example 55. Whole Cell Extract Tdp2 Assay

DT40 knockout cells ($1 \times 10^7$) for Tdp1 (TDP1-/-) complemented with human TDP2 (hTDP2) were collected, washed, and centrifuged. Cell pellets were then lysed and stored similarly to hTDP1 extracts (see above). The 18-mer single-stranded oligonucleotide was incubated at 1 nM with 4 μg/mL of whole cell extracts in the absence or presence of inhibitor for 15 min at room temperature in the WCE buffer containing 50 mM Tris HCl, pH 7.5, 80 mM KCl, 5 mM MgCl$_2$, 2 mM EDTA, 1 mM DTT, 40 μg/mL BSA, and 0.01% Tween-20. Reactions were terminated by the addition of 1 volume of gel loading buffer [99.5% (v/v) formamide, 5 mM EDTA, 0.01% (w/v) xylene cyanol, and 0.01% (w/v) bromophenol blue]. Samples were then treated and run similarly to the hTDP1 whole cell extract (Example 51).

Example 56. Additional Compounds

Table 1 shows compounds of compounds 1 to 44 and additional compounds 59-74. All compounds were prepared by the methods shown in Examples 1 to 50. Routine changes in starting materials and reaction conditions, readily apparent to those of skill in the art, were used to make the particular compounds disclosed in Table 1. 4 stars "**" is used to denote compounds with an IC$_{50}$≤1 micromolar, 3 stars "*" indicates a compound with 1 micromolar<IC$_{50}$≤12 micromolar, 2 stars "**" denotes compounds with 12 micromolar<IC$_{50}$≤37 micromolar, one star "*" denotes compounds with 37 micromolar<IC$_{50}$≤111 micromolar, and 0 indicates a compound with IC$_{50}$>111 micromolar. A standard Tdp2 inhibition assay, such as the assay of Example 53, is used to determine the IC$_{50}$'s for the compounds. LC methods are given in the General Methods section.

TABLE 1

Characterization and Enzymatic Inhibition Data for Selected Compounds

| Cpd | Structure | REC TDP2 (μM) | WCE hTDP2 (μM) | LC retention (method, time in min) | HRMS |
|---|---|---|---|---|---|
| 1 | 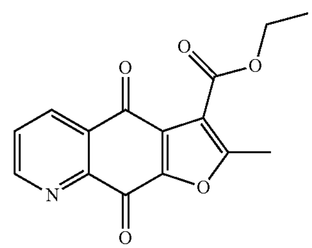 [SMILES: CCOC(=O)c1c(C)oc2c1C(=O)c1cccnc1C2=O] | * | * | A 8.2 | 284.0574 |
| 2 | 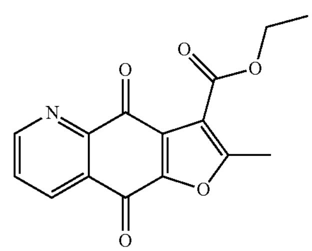 [SMILES: CCOC(=O)c1c(C)oc2c1C(=O)c1ncccc1C2=O] | * |  | A 8.4 | 284.0551 |
| 3 | 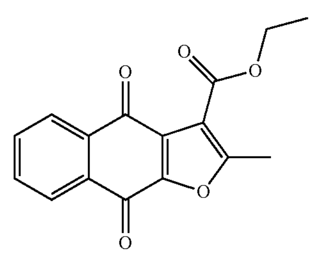 [SMILES: CCOC(=O)c1c(C)oc2c1C(=O)c1ccccc1C2=O] | * | Not tested | A 18.0 | 307.0590 |
| 4 | 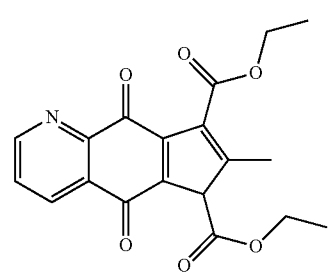 [SMILES: CCOC(=O)C1=C(C)C(C(=O)OCC)C2=C1C(=O)c1ncccc1C2=O] | 0 | Not tested | A 21.8 | NT |

TABLE 1-continued

Characterization and Enzymatic Inhibition Data for Selected Compounds

| Cpd | Structure | REC TDP2 (µM) | WCE hTDP2 (µM) | LC retention (method, time in min) | HRMS |
|---|---|---|---|---|---|
| 5 | 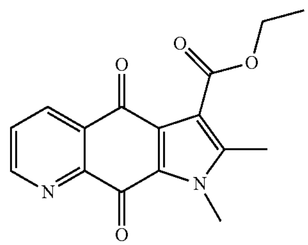 [SMILES: CCOC(=O)c1c2c(n(C)c1C)C(=O)c1ncccc1C2=O] | 0 | Not tested | A 8.4 | NT |
| 6 | 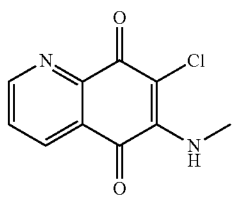 | 0 | Not tested | NT | NT |
| 7 | 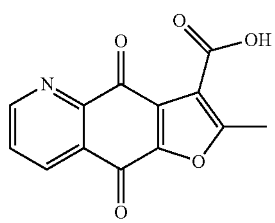 [SMILES: Cc1oc2c(c1C(=O)O)C(=O)c1ncccc1C2=O] | * | * | C 6.7 | NT |
| 8 | 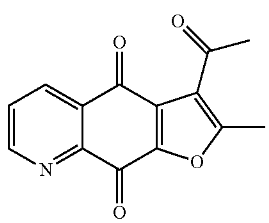 [SMILES: CC(=O)c1c(C)oc2c1C(=O)c1cccnc1C2=O] | 0 | Not tested | A 7.4 | 256.0593 |
| 9 | 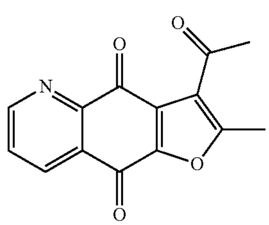 [SMILES: CC(=O)c1c(C)oc2c1C(=O)c1ncccc1C2=O] | * | * | A 7.3 | 256.0613 |
| 10 | 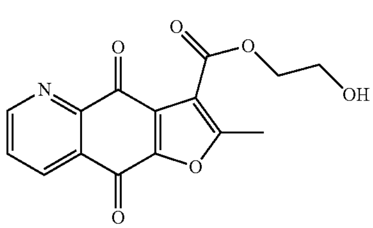 [SMILES: Cc1oc2c(c1C(=O)OCCO)C(=O)c1ncccc1C2=O] |  | * | B 6.0 | 300.0499 |

TABLE 1-continued

Characterization and Enzymatic Inhibition Data for Selected Compounds

| Cpd | Structure | REC TDP2 (μM) | WCE hTDP2 (μM) | LC retention (method, time in min) | HRMS |
|---|---|---|---|---|---|
| 11 | 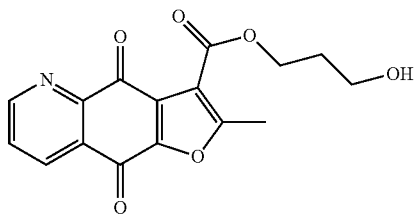 [SMILES: Cc1oc2c(c1C(=O)OCCCO)C(=O)c1ncccc1C2=O] |  | * | B 8.0 | 314.0653 |
| 12 | 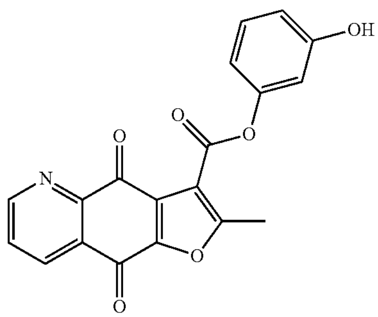 |  | * | C 9.0 | 348.0499 |
| 13 | 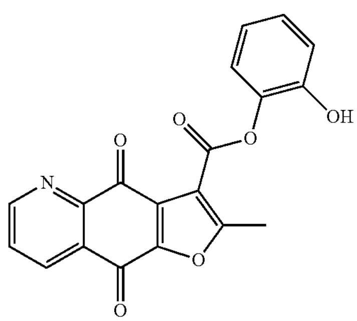 [SMILES: Cc1oc2c(c1C(=O)Oc1ccccc1O)C(=O)c1ncccc1C2=O] |  | * | C 9.4 | 348.0514 |
| 14 | 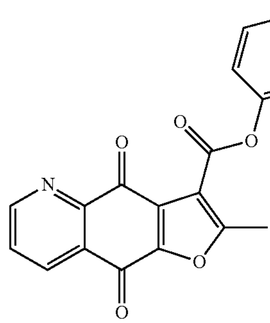 |  | * | B 11.0 | 332.0563 |
| 15 | 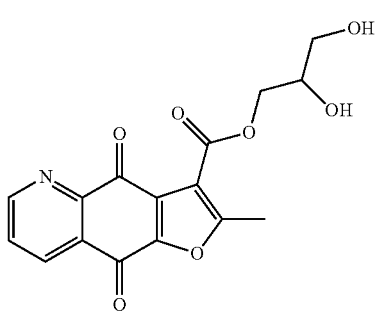 [SMILES: Cc1oc2c(c1C(=O)OCC(O)CO)C(=O)c1ncccc1C2=O] |  | * | B 7.3 | 330.0604 |

TABLE 1-continued

Characterization and Enzymatic Inhibition Data for Selected Compounds

| Cpd | Structure | REC TDP2 (μM) | WCE hTDP2 (μM) | LC retention (method, time in min) | HRMS |
|---|---|---|---|---|---|
| 16 | 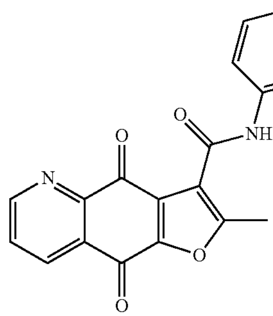 | 0 | Not tested | A 8.5 | 331.0723 |
| 17 | 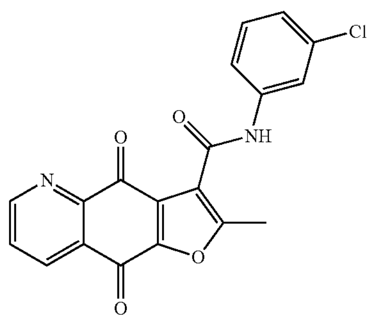 [SMILES: Cc1oc2c(c1C(=O)Nc1cccc(Cl)c1)C(=O)c1ncccc1C2=O] | 0 | Not tested | A 7.6 | 367.0501 |
| 18 | 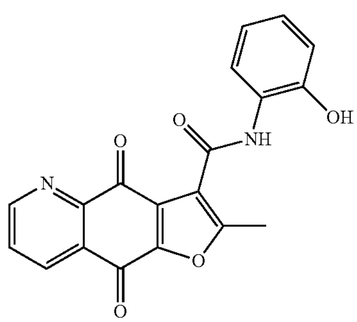 [SMILES: Cc1oc2c(c1C(=O)Nc1ccccc1O)C(=O)c1ncccc1C2=O] | 0 | Not tested | A 6.8 | 347.0656 |
| 19 | 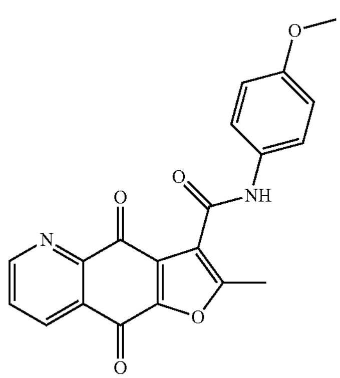 [SMILES: COc1ccc(NC(=O)c2c(C)oc3c2C(=O)c2ncccc2C3=O)cc1] | 0 | Not tested | A 10.5 | 361.0817 |

TABLE 1-continued

Characterization and Enzymatic Inhibition Data for Selected Compounds

| Cpd | Structure | REC TDP2 (μM) | WCE hTDP2 (μM) | LC retention (method, time in min) | HRMS |
|---|---|---|---|---|---|
| 20 | 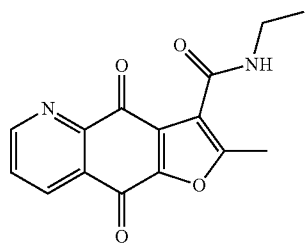 [SMILES: CCNC(=O)c1c(C)oc2c1C(=O)c1ncccc1C2=O] | 0 | Not tested | A 7.5 | 307.0699 |
| 21 | 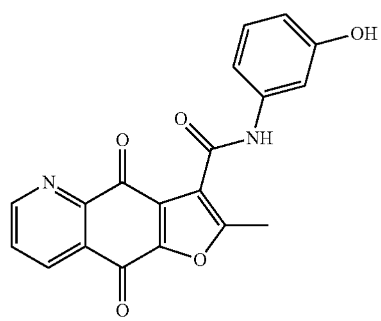 [SMILES: Cc1oc2c(c1C(=O)Nc1cccc(O)c1)C(=O)c1ncccc1C2=O] | 0 | Not tested | A 8.0 | NT |
| 22 | 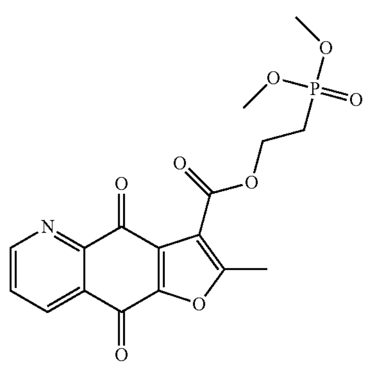 [SMILES: COP(=O)(CCOC(=O)c1c(C)oc2c1C(=O)c1ncccc1C2=O)OC] | * |  | B 8.1 | 392.0538 |
| 23 | 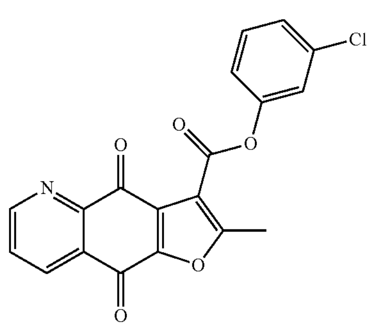 [SMILES: Cc1oc2c(c1C(=O)Oc1cccc(Cl)c1)C(=O)c1ncccc1C2=O] |  | * | B 13.0 | 368.0341 |

TABLE 1-continued

Characterization and Enzymatic Inhibition Data for Selected Compounds

| Cpd | Structure | REC TDP2 (μM) | WCE hTDP2 (μM) | LC retention (method, time in min) | HRMS |
|---|---|---|---|---|---|
| 24 | 2-chlorophenyl ester derivative | *** | ** | B 10.5 | 368.0335 |
| 25 | 2-naphthyl ester derivative | 0 | Not tested | B 15.4 | 382.0706 |
| 26 | 3-cyanophenyl ester derivative | *** | *** | C 7.7 | 359.0679 |
| 27 | 4-chlorophenyl ester derivative | *** | *** | B 13.6 | 368.0334 |

TABLE 1-continued

Characterization and Enzymatic Inhibition Data for Selected Compounds

| Cpd | Structure | REC TDP2 (µM) | WCE hTDP2 (µM) | LC retention (method, time in min) | HRMS |
|---|---|---|---|---|---|
| 28 | 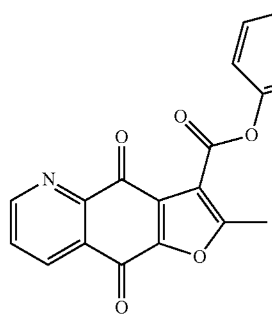 | * | * | C 5.9 | 335.0673 |
| 29 | 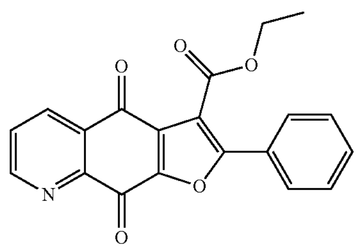 [SMILES: CCOC(=O)c1c(-c2ccccc2)oc2c1C(=O)c1cccnc1C2=O] | * | ** | A 13.9 | 348.0865 |
| 30 | 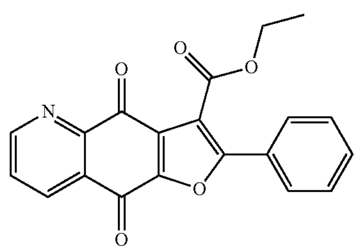 [SMILES: CCOC(=O)c1c(-c2ccccc2)oc2c1C(=O)c1ncccc1C2=O] |  |  | A 14.6 | 348.0887 |
| 31 | 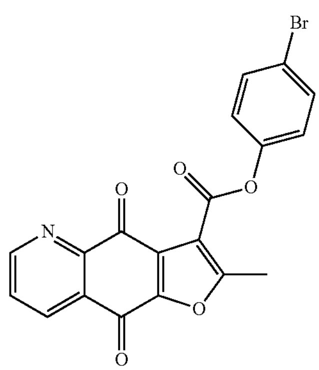 |  |  | A 15.2 | 411.9820 |
| 32 | 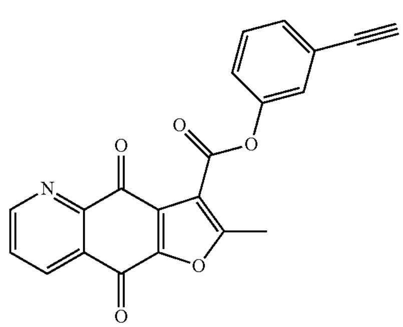 [SMILES: C#Cc1cccc(OC(=O)c2c(C)oc3c2C(=O)c2ncccc2C3=O)c1] | * | ** | A 10.3 | 380.0543 |

TABLE 1-continued

Characterization and Enzymatic Inhibition Data for Selected Compounds

| Cpd | Structure | REC TDP2 (µM) | WCE hTDP2 (µM) | LC retention (method, time in min) | HRMS |
|---|---|---|---|---|---|
| 33 | 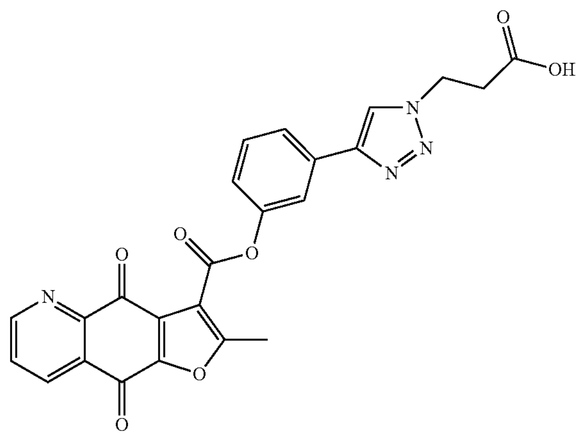 [SMILES: Cc1oc2c(c1C(=O)Oc1cccc(-c3cn(CCC(=O)O)nn3)c1)C(=O)c1ncccc1C2=O] |  |  | A 6.1 | 471.0920 |
| 34 | 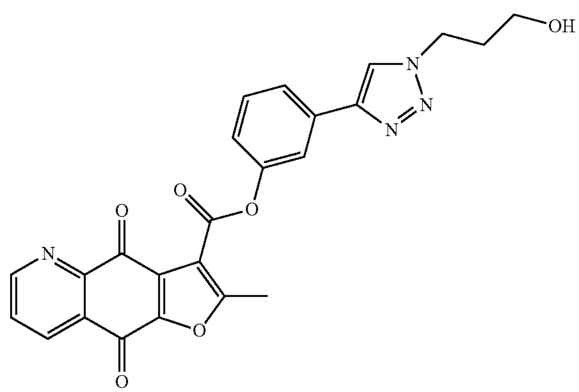 [SMILES: Cc1oc2c(c1C(=O)Oc1cccc(-c3cn(CCCO)nn3)c1)C(=O)c1ncccc1C2=O] | * | * | C 10.1 | 457.1138 |
| 35 | 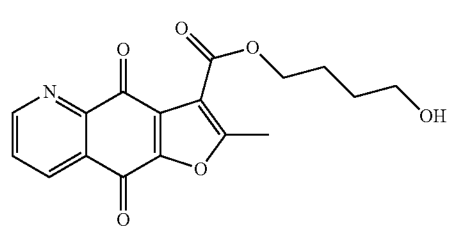 [SMILES: Cc1oc2c(c1C(=O)OCCCCO)C(=O)c1ncccc1C2=O] |  | * | A 10.4 | 352.0792 |
| 36 | 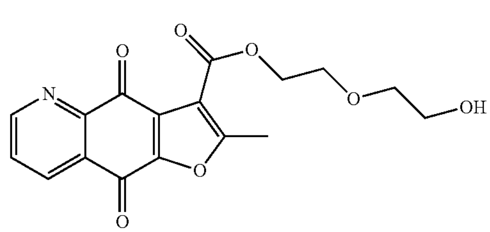 [SMILES: Cc1oc2c(c1C(=O)OCCOCCO)C(=O)c1ncccc1C2=O] |  |  | A 8.8 | 368.0752 |

TABLE 1-continued

Characterization and Enzymatic Inhibition Data for Selected Compounds

| Cpd | Structure | REC TDP2 (μM) | WCE hTDP2 (μM) | LC retention (method, time in min) | HRMS |
|---|---|---|---|---|---|
| 37 | 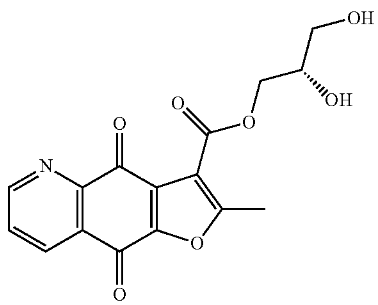 [SMILES: Cc1oc2c(c1C(=O)OC[C@@H](O)CO)C(=O)c1ncccc1C2=O] | * |  | A 9.3 | NT |
| 38 | 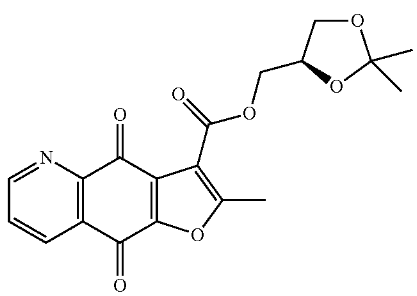 [SMILES: Cc1oc2c(c1C(=O)OC[C@H]1COC(C)(C)O1)C(=O)c1ncccc1C2=O] | * | * | A 14.9 | 394.0909 |
| 39 | 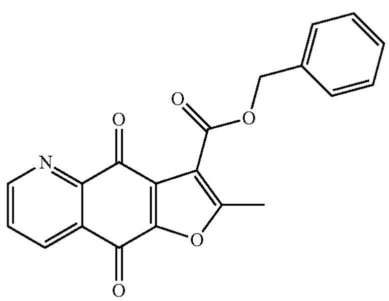 [SMILES: Cc1oc2c(c1C(=O)OCc1ccccc1)C(=O)c1ncccc1C2=O] | NT | NT | A 23.7 | 370.0704 |
| 40 | 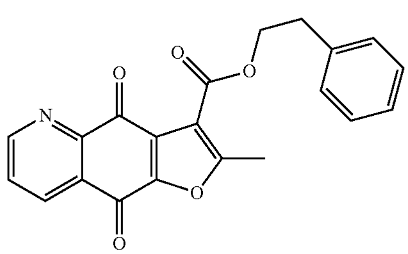 [SMILES: Cc1oc2c(c1C(=O)OCCc1ccccc1)C(=O)c1ncccc1C2=O] | * | ** | A 14.9 | 384.0864 |
| 41 | 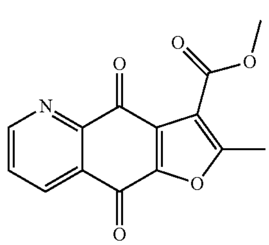 [SMILES: COC(=O)c1c(C)oc2c1C(=O)c1ncccc1C2=O] |  | * | A 7.1 | NT |

TABLE 1-continued

Characterization and Enzymatic Inhibition Data for Selected Compounds

| Cpd | Structure | REC TDP2 (μM) | WCE hTDP2 (μM) | LC retention (method, time in min) | HRMS |
|---|---|---|---|---|---|
| 42 | 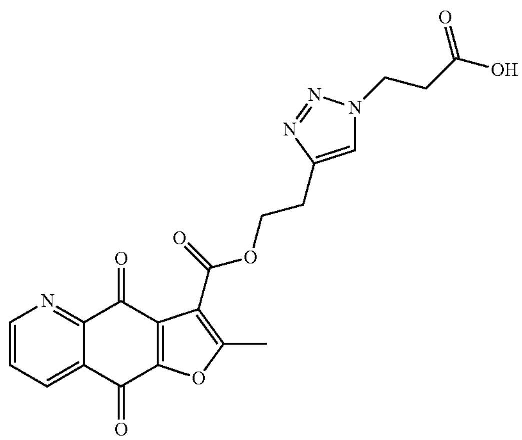 [SMILES: Cc1oc2c(c1C(=O)OCCc1cn(CCC(=O)O)nn1)C(=O)c1ncccc1C2=O] |  |  | A 9.7 | 423.0923 |
| 43 | 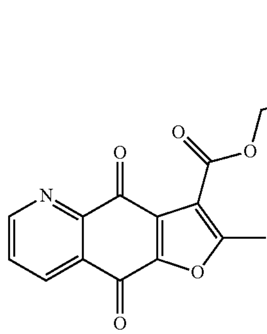 |  |  | A 11.2 | 332.0544 |
| 44 | 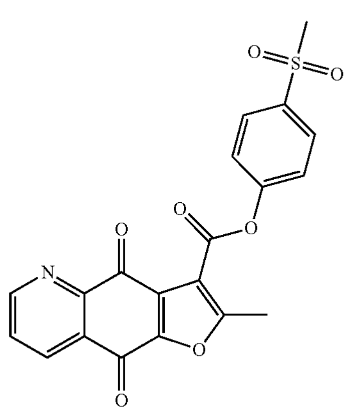 [SMILES: Cc1oc2c(c1C(=O)Oc1ccc(S(C)(=O)=O)cc1)C(=O)c1ncccc1C2=O] |  |  | A 9.3 | 434.0334 |

TABLE 1-continued

Characterization and Enzymatic Inhibition Data for Selected Compounds

| Cpd | Structure | REC TDP2 (μM) | WCE hTDP2 (μM) | LC retention (method, time in min) | HRMS |
|---|---|---|---|---|---|
| 59 | 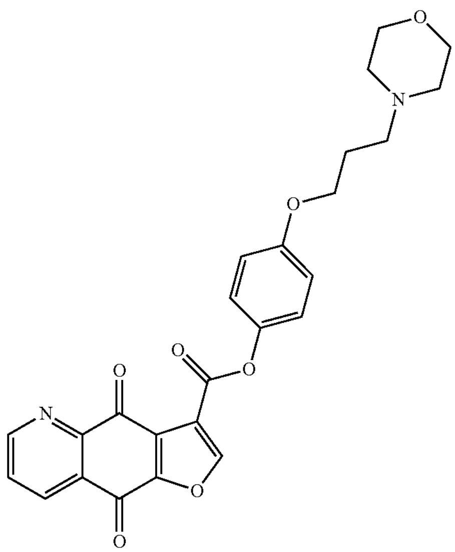 [SMILES: O=C(Oc1ccc(OCCCN2CCOCC2)cc1)c1coc2c1C(=O)c1ncccc1C2=O] | * | *** | | |
| 60 | 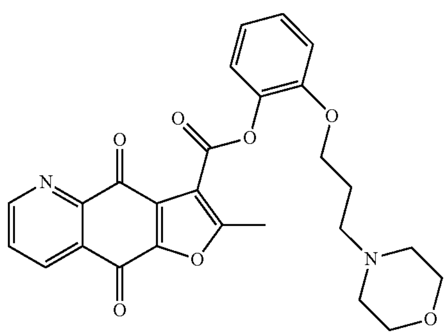 [SMILES: Cc1oc2c(c1C(=O)Oc1ccccc1OCCCN1CCOCC1)C(=O)c1ncccc1C2=O] | * | *** | | |
| 61 | 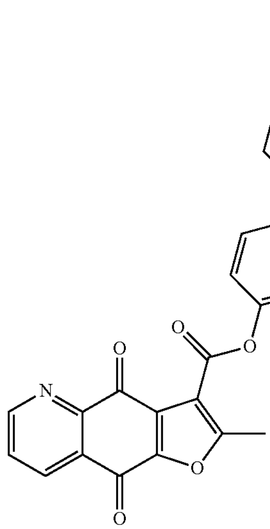 | * | *** | | |

TABLE 1-continued
Characterization and Enzymatic Inhibition Data for Selected Compounds
| Cpd | Structure | REC TDP2 (µM) | WCE hTDP2 (µM) | LC retention (method, time in min) | HRMS |
|---|---|---|---|---|---|
| 62 | 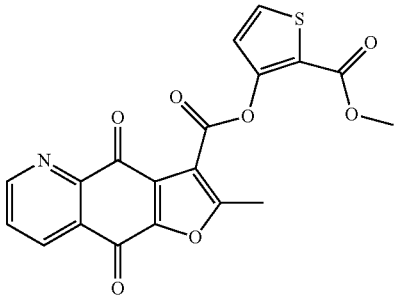 [SMILES: COC(=O)c1sccc1OC(=O)c1c(C)oc2c1C(=O)c1ncccc1C2=O] |  | * | | |
| 63 | 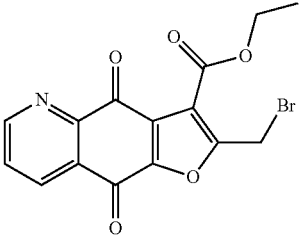 [SMILES: CCOC(=O)c1c(CBr)oc2c1C(=O)c1ncccc1C2=O] |  | * | | |
| 64 | 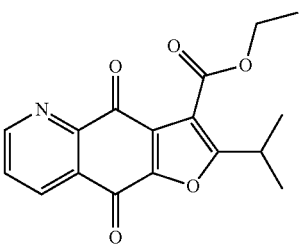 [SMILES: CCOC(=O)c1c(C(C)C)oc2c1C(=O)c1ncccc1C2=O] |  | ** | | |
| 65 | 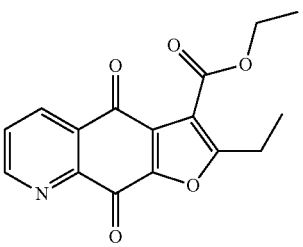 [SMILES: CCOC(=O)c1c(CC)oc2c1C(=O)c1cccnc1C2=O] | * | Not tested | | |
| 66 | 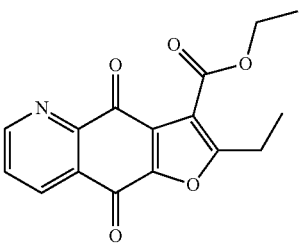 [SMILES: CCOC(=O)c1c(CC)oc2c1C(=O)c1ncccc1C2=O] | ** | Not tested | | |

TABLE 1-continued
Characterization and Enzymatic Inhibition Data for Selected Compounds
| Cpd | Structure | REC TDP2 (μM) | WCE hTDP2 (μM) | LC retention (method, time in min) | HRMS |
|---|---|---|---|---|---|
| 67 | 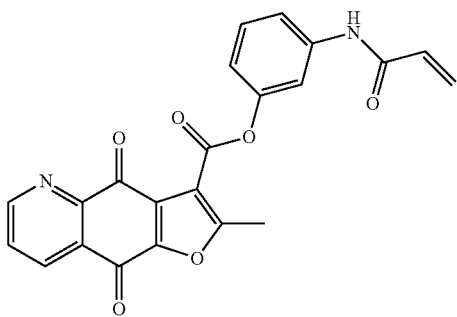 [SMILES: C=CC(=O)Nc1cccc(OC(=O)c2c(C)oc3c2C(=O)c2ncccc2C3=O)c1] | ** | Not tested | | |
| 68 | 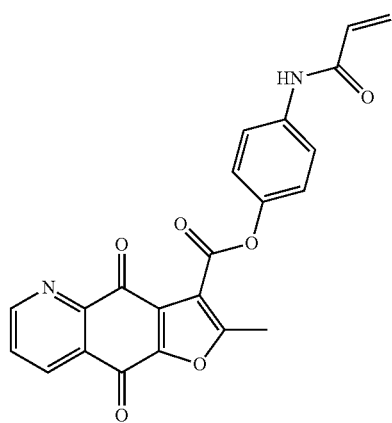 [SMILES: C=CC(=O)Nc1ccc(OC(=O)c2c(C)oc3c2C(=O)c2ncccc2C3=O)cc1] | ** | Not tested | | |
| 69 | 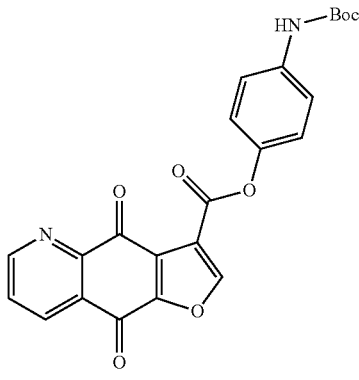 [SMILES: CC(C)(C)OC(=O)Nc1ccc(OC(=O)c2coc3c2C(=O)c2ncccc2C3=O)cc1] | ** | Not tested | | |
| 70 | 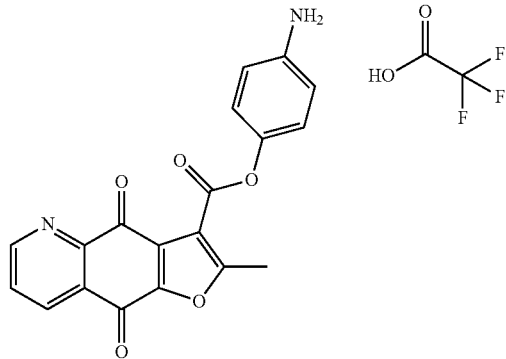 [SMILES: Cc1oc2c(c1C(=O)Oc1ccc(N)cc1)C(=O)c1ncccc1C2=O ; O=C(O)C(F)(F)F] | *** | Not tested | | |

TABLE 1-continued

Characterization and Enzymatic Inhibition Data for Selected Compounds

| Cpd | Structure | REC TDP2 (μM) | WCE hTDP2 (μM) | LC retention (method, time in min) | HRMS |
|---|---|---|---|---|---|
| 71 | 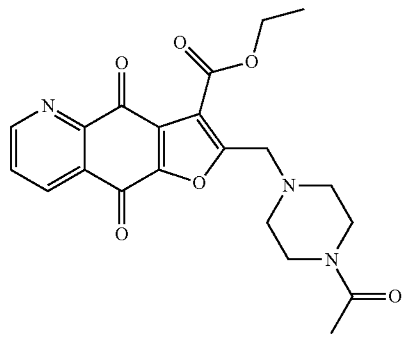 [SMILES: CCOC(=O)c1c(CN2CCN(C(C)=O)CC2)oc2c1C(=O)c1ncccc1C2=O] | ** | Not tested | | |
| 72 | 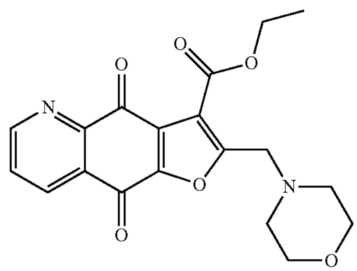 [SMILES: CCOC(=O)c1c(CN2CCOCC2)oc2c1C(=O)c1ncccc1C2=O] | *** | Not tested | | |
| 73 | 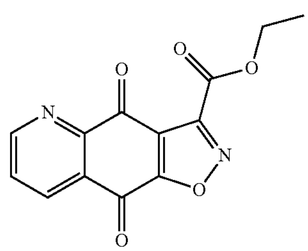 [SMILES: CCOC(=O)c1noc2c1C(=O)c1ncccc1C2=O] | **** | Not tested | | |
| 74 | 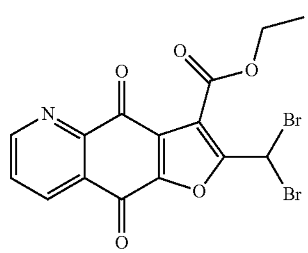 | ** | Not tested | | |

What is claimed is:

1. A compound or pharmaceutically acceptable salt thereof of Formula I:

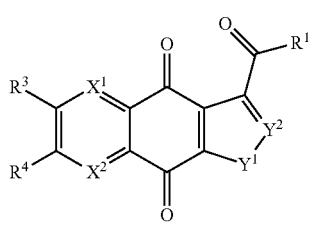

Formula I wherein $X^1$ is N;

$X^2$ is $CR^6$; and $R^1$ is $C_2$-$C_6$alkenyloxy, or $C_3$-$C_7$cycloalkyloxy, where one or more methylene units in the alkenyl, or alkynyl portion of $R^1$ is optionally and independently replaced with —O—, —S—, or —N($R^7$)—, and $R^1$ is substituted by 0-3 substituents independently chosen at each occurrence from halogen, hydroxyl, cyano, =N, =NOR$^7$, —CO$_2$H, —(CO)—O—$C_1$-$C_6$alkyl, —C(O)NR$^7$R$^8$, and —W—P(O)YR$^9$ZR$^{10}$, or $R^1$ is —O-A-B wherein O is an oxygen atom;

A is a linker consisting of a bond, an alkylene chain of 1 to 6 carbons, or a phenylene group;

B is a phenyl, or a 5 or 6 membered heterocycle having 1, 2, or 3 ring atoms independently chosen from N, O, and S, wherein B is substituted with 0-3 substituents independently chosen from halogen, hydroxyl, cyano, amino, —SH, $C_1$-$C_6$alkyl, $C_2$-$C_6$alkenyl, $C_2$-$C_6$alkynyl, $C_1$-$C_6$alkoxy, $C_2$-$C_6$alkanoyl, $C_1$-$C_6$thioalkyl, $C_1$-$C_6$haloalkyl, $C_1$-$C_6$haloalkoxy, —($C_0$-$C_6$alkyl)cycloalkyl, —($C_0$-$C_6$alkyl)$CO_2$H, —($C_0$-$C_6$alkyl)-(CO)—O—$C_1$-$C_6$alkyl, —($C_0$-$C_6$alkyl)C(O)NR$^7$R$^8$, —($C_0$-$C_6$alkyl)NR$^7$C(O)R$^8$, —($C_1$-$C_6$alkyl)alkoxy, —($C_1$-$C_6$alkyl)OH, —($C_0$-$C_6$alkyl)NR$^7$R$^8$, —$SO_2$—$C_1$-$C_6$alkyl, and —($C_0$-$C_6$alkyl)-W—P(O)YR$^9$ZR$^{10}$;

$Y^1$ is O;

$Y^2$ is N or C-R$^2$;

R$^2$ is halogen, $C_1$-$C_6$alkyl, $C_1$-$C_6$alkoxy, $C_1$-$C_6$haloalkyl, $C_1$-$C_6$haloalkoxy, —($C_0$-$C_6$alkyl)cycloalkyl, —($C_0$-$C_6$alkyl)NR$^7$R$^8$, or phenyl, each R$^2$ other than halogen being substituted with 0 to 3 groups chosen independently at each occurrence from halogen, hydroxyl, $C_1$-$C_6$alkyl, $C_1$-$C_6$alkoxy, $C_1$-$C_6$haloalkyl, and $C_1$-$C_6$haloalkoxy; or W, Y, and Z are independently at each occurrence a bond or O;

R$^3$, R$^4$, and R$^6$, are chosen independently at each occurrence from hydrogen, halogen, cyano, amino, $C_1$-$C_6$alkyl, —($C_0$-$C_6$alkyl)cycloalkyl, $C_1$-$C_6$alkoxy, $C_1$-$C_6$haloalkyl, and $C_1$-$C_6$haloalkoxy;

R$^7$, R$^8$, R$^9$ and R$^{10}$ are chosen independently at each occurrence from hydrogen, $C_1$-$C_6$alkyl, $C_2$-$C_6$alkenyl, —($C_0$-$C_6$alkyl)cycloalkyl, and $C_1$-$C_6$haloalkyl, and any R$^7$ and R$^8$ bound to the same nitrogen atom may be taken together to form a 4- to 7-membered heterocycloalkyl group substituted with 0 to 2 substituents chosen from hydroxyl, halogen, $C_1$-$C_4$alkyl, $C_1$-$C_4$alkoxy, and $C_2$-$C_4$alkanoyl; and R$^{11}$ is $C_1$-$C_6$alkyl or $C_1$-$C_6$alkylamino.

2. The compound or salt of claim 1 wherein

R$^1$ is —($C_0$-$C_6$alkyl)cycloalkyl, in which one or more methylene units in the alkoxy or alkyl portion of R$^1$ is optionally and independently replaced with with —O—, or —N(R$^7$)—, and R$^1$ is substituted by 0-3 substituents independently chosen at each occurrence from hydroxyl, halogen, cyano, —$CO_2$H, —(CO)—O—$C_1$-$C_6$alkyl, and —W—P(O)YR$^9$ZR$^{10}$; or R$^1$ is the group —O-A-B;

B is a phenyl, or a 5 or 6 membered heteroaryl having 1, 2, or 3 ring atoms wherein B is substituted with 0-3 substituents independently chosen from halogen, hydroxyl, cyano, amino, $C_1$-$C_6$alkyl, $C_2$-$C_6$alkenyl, $C_2$-$C_6$alkynyl, $C_1$-$C_6$alkoxy, $C_1$-$C_6$haloalkyl, $C_1$-$C_6$haloalkoxy, —($C_0$-$C_6$alkyl)cycloalkyl, —($C_0$-$C_6$alkyl)$CO_2$H, —($C_0$-$C_6$alkyl)-(CO)—O—$C_1$-$C_6$alkyl, —($C_1$-$C_6$alkyl)alkoxy, —($C_1$-$C_6$alkyl)OH, —$SO_2$—$C_1$-$C_6$alkyl, and —($C_0$-$C_6$alkyl)-W—P(O)YR$^9$ZR$^{10}$;

R$^2$ is halogen, $C_1$-$C_6$alkyl, $C_1$-$C_6$haloalkyl, —($C_0$-$C_6$alkyl)cycloalkyl, or phenyl, said phenyl being substituted with 0 to 3 groups chosen independently at each occurrence from halogen, hydroxyl, $C_1$-$C_6$alkyl, $C_1$-$C_6$alkoxy, $C_1$-$C_6$haloalkyl, and $C_1$-$C_6$haloalkoxy; and R$^3$ and R$^4$ are both hydrogen.

3. The compound or salt of claim 1, wherein

R$^2$ is halogen, $C_1$-$C_6$alkyl, $C_1$-$C_6$alkoxy, $C_1$-$C_6$haloalkyl, $C_1$-$C_6$haloalkoxy, —($C_0$-$C_6$alkyl)cycloalkyl, —($C_0$-$C_6$alkyl) NR$^7$R$^8$, or phenyl, each R$^2$ other than hydrogen and halogen being substituted with 0 to 3 groups chosen independently at each occurrence from halogen, hydroxyl, $C_1$-$C_6$alkyl, $C_1$-$C_6$alkoxy, $C_1$-$C_6$haloalkyl, and $C_1$-$C_6$haloalkoxy.

4. The compound or salt of claim 1 wherein

R$^1$ is substituted with at least one —W—P(O)YR$^9$ZR$^{10}$ substituent; and

W is a bond; and Y and Z are both O.

5. The compound or salt of any claim 2 wherein R$^2$ is methyl or phenyl.

6. The compound or salt of claim 1 wherein $X^2$ is CH.

7. The compound or salt of claim 1 wherein

R$^1$ is a phenoxy or pyridyloxy, each of which is optionally substituted with 0-3 substituents independently chosen from halogen, hydroxyl, cyano, $C_1$-$C_6$alkyl, $C_2$-$C_6$alkenyl, $C_2$-$C_6$alkynyl, $C_1$-$C_6$alkoxy, $C_1$-$C_6$haloalkyl, $C_1$-$C_6$haloalkoxy, —($C_0$-$C_6$alkyl)cycloalkyl, —($C_0$-$C_6$alkyl)$CO_2$H, —($C_0$-$C_6$alkyl)-(CO)—O—$C_1$-$C_6$alkyl, —($C_1$-$C_6$alkyl)alkoxy, —($C_1$-$C_6$alkyl)OH, —$SO_2$—$C_1$-$C_6$alkyl, and —($C_0$-$C_6$alkyl)-W—P(O)YR$^9$ZR$^{10}$.

8. The compound or salt of claim 1, wherein R$^1$ is —O-A-B, wherein

A is a bond or an alkylene chain of 1 to 3 carbon atoms; and

B is phenyl or pyridyl optionally substituted with 0-3 substituents independently chosen from halogen, hydroxyl, cyano, $C_1$-$C_4$alkyl, $C_1$-$C_4$alkoxy, $C_2$-$C_4$alkanoyl, $C_1$-$C_2$haloalkyl, $C_1$-$C_2$haloalkoxy, —($C_0$-$C_2$alkyl)-(CO)—O—$C_1$-$C_6$alkyl, —($C_0$-$C_2$alkyl)C(O)NR$^7$R$^8$, —($C_1$-$C_6$alkyl)NR$^7$C(O)R$^8$, —($C_1$-$C_6$alkyl)OH, and —$SO_2$—$C_1$-$C_2$alkyl.

9. The compound or salt of claim 1, wherein

R$^1$ is —O-A-B, wherein

A is a bond or an alkylene chain of 1 to 3 carbon atoms; and

B is a triazolyl, pyrazolyl, imidazolyl, thienyl, dioxylanyl, morpholinyl, piperazinyl, or piperidinyl group;

each of which B is substituted with 0-3 substituents independently chosen from halogen, hydroxyl, cyano, amino, $C_1$-$C_6$alkyl, $C_2$-$C_6$alkenyl, $C_2$-$C_6$alkynyl, $C_1$-$C_6$alkoxy, $C_2$-$C_6$alkanoyl, $C_1$-$C_2$haloalkyl, $C_1$-$C_2$haloalkoxy, —($C_0$-$C_6$alkyl) $CO_2$H, —($C_0$-$C_6$alkyl)-(CO)—O—$C_1$-$C_6$alkyl, —($C_0$-C6alkyl)C(O)NR$^7$R$^8$, —($C_0$-$C_6$alkyl)NR$^7$C(O)R$^8$, —($C_1$-$C_6$alkyl)OH, —($C_0$-$C_6$alkyl) NR$^7$R$^8$, and —$SO_2$—$C_1$-$C_6$alkyl; where R$^7$ and R$^8$ are hydrogen or $C_1$-$C_4$alkyl.

10. The pharmaceutical composition comprising a compound or salt of claim 1, together with a pharmaceutically acceptable carrier.

11. The method of treating cancer by inhibiting tyrosyl-DNA phosphodiesterase 2, comprising administering a therapeutically effective amount of a compound or salt of claim 1, to a patient in need of such treatment.

12. The method of claim 11, additionally comprising administering the compound of claim 1 in combination with one or more additional compounds, wherein at least one of the additional compounds is an active agent known to be an inhibitor of topoisomerase 2, to a patient in need of such treatment.

13. The method of claim 11, additionally comprising administering a therapeutically effective amount of a compound or salt of claim 1, in combination with one or more additional compounds, wherein at least one additional compound is an active agent chosen from etoposide, teniposide, doxorubicin, daunorubicin, mitoxantrone, amsacrine, ellipticines, aurintricarboxylic acid, and 3-hydroxy-2-[(1R)-6-isopropenyl-3-methyl-cyclohex-2-en-1-yl]-5-pentyl-1,4-benzoquinone (HU-331), to a patient in need of such treatment.

14. The method of claim 11, wherein the cancer is glioma, acute myelogenous leukemia, acute myeloid leukemia, myelodysplastic/myeloproliferative neoplasms, sarcoma, chronic myelomonocytic leukemia, non-Hodgkin's lymphoma, astrocytoma, melanoma, non-small cell lung cancer, small cell lung cancer, cervical cancer, rectal cancer, ovarian cancer, cholangiocarcinomas, chondrosarcoma, or colon cancer.

15. A compound or salt, wherein the compound is

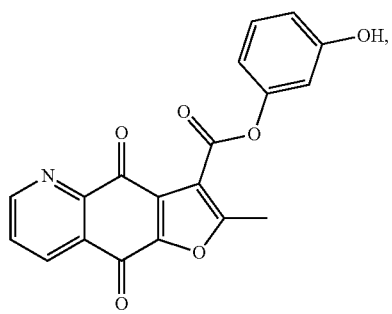

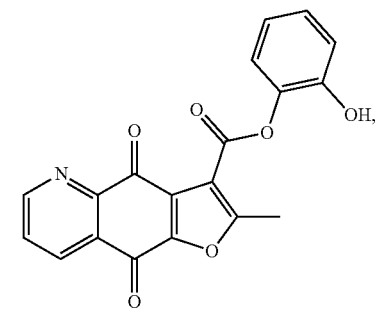

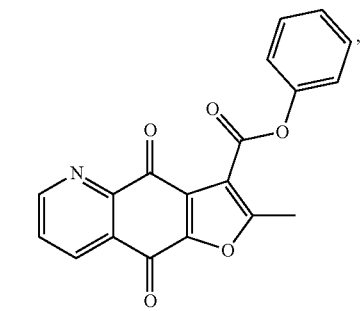

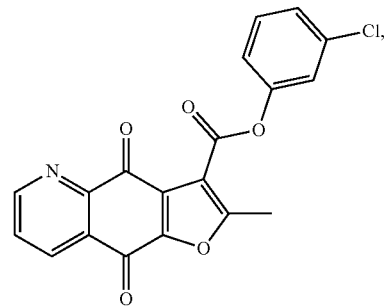

-continued

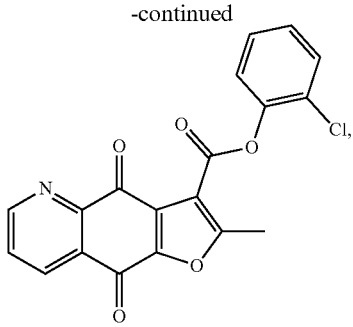

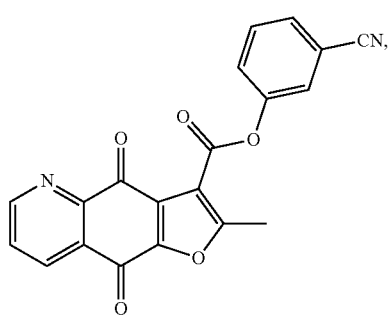

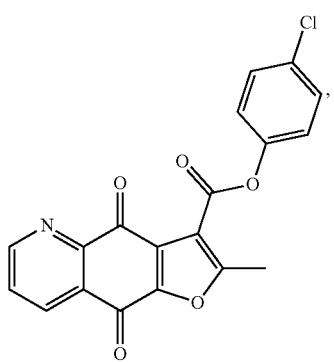

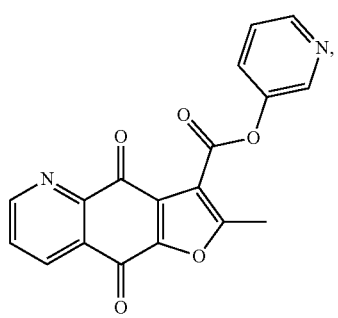

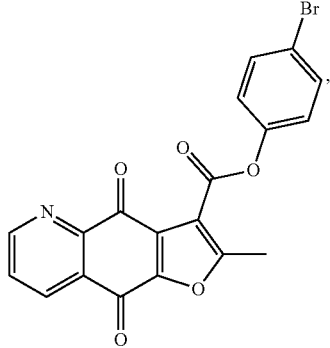

73
-continued
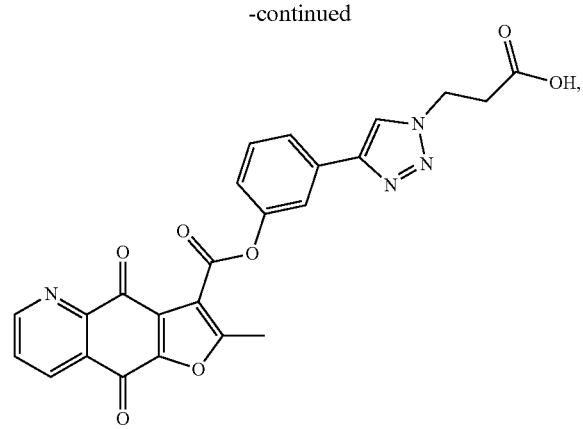
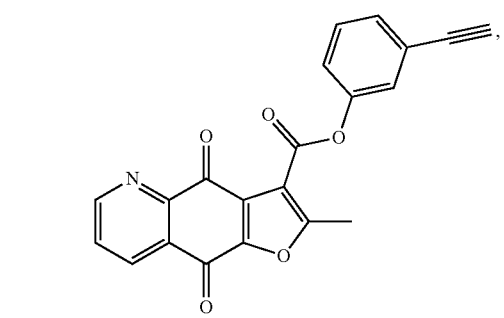
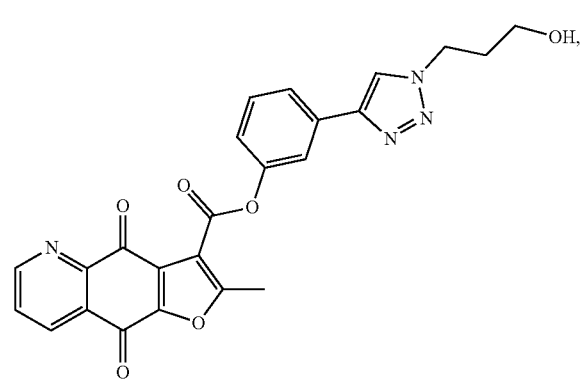
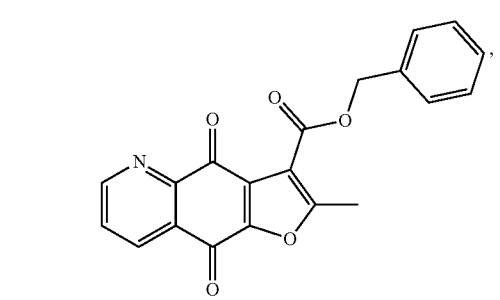
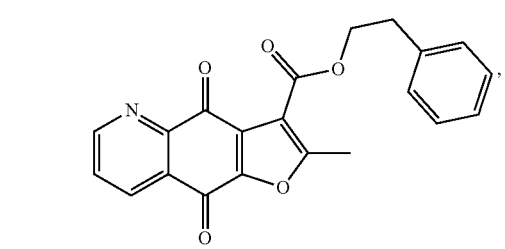
74
-continued
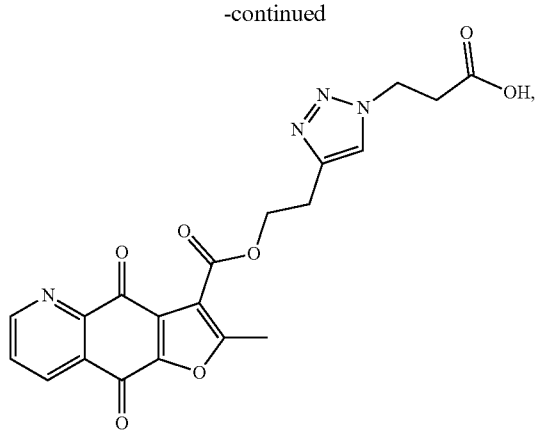
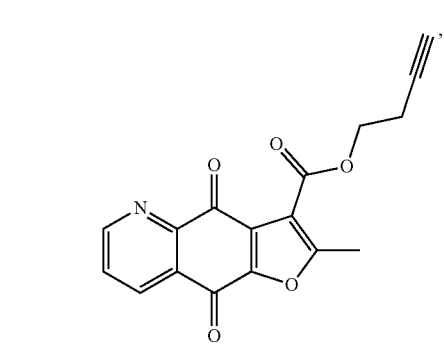
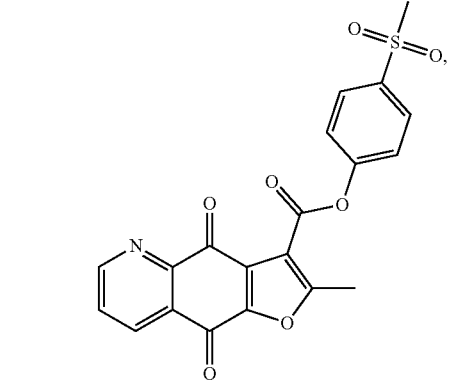
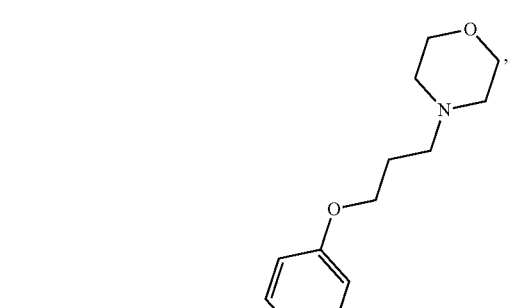
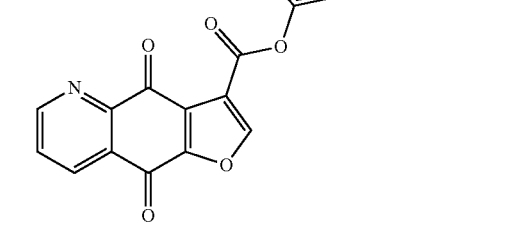

-continued

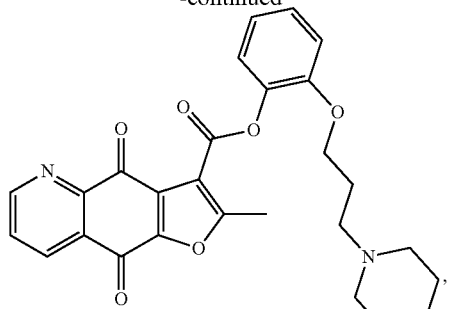

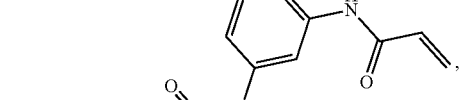

-continued

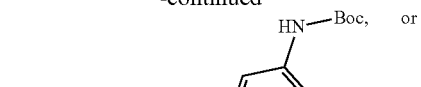

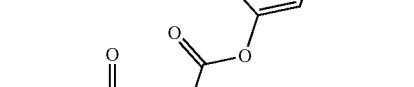

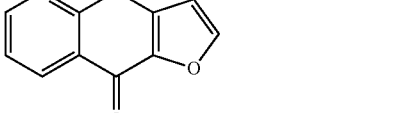

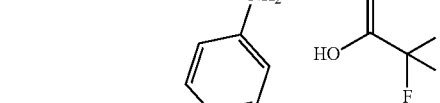

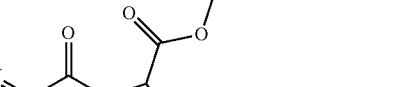

16. The compound or salt of claim 1, wherein

R$^1$ is —O-A-B wherein

O is an oxygen atom;

A is a linker consisting of a bond, an alkylene chain of 1 to 6 carbons, or a phenylene group;

B is a phenyl, or a 5 or 6 membered heterocycle having 1, 2, or 3 ring atoms independently chosen from N, O, and S, wherein B is substituted with 0-3 substituents independently chosen from halogen, hydroxyl, cyano, amino, —SH, C$_1$-C$_6$alkyl, C$_2$-C$_6$alkenyl, C$_2$-C$_6$alkynyl, C$_1$-C$_6$alkoxy, C$_2$-C$_6$alkanoyl, C$_1$-C$_6$thioalkyl, C$_1$-C$_6$haloalkyl, C$_1$-C$_6$haloalkoxy, —(C$_0$-C$_6$alkyl)cycloalkyl, —(C$_0$-C$_6$alkyl)CO$_2$H, —(C$_0$-C$_6$alkyl)-(CO)—O—C$_1$-C$_6$alkyl, —(C$_0$-C$_6$alkyl)C(O)NR$^7$R$^8$, —(C$_0$-C$_6$alkyl)NR$^7$C(O)R$^8$, —(C$_1$-C$_6$alkyl)alkoxy, —(C$_1$-C$_6$alkyl)OH, —(C$_0$-C$_6$alkyl)NR$^7$R$^8$, —SO$_2$—C$_1$-C$_6$alkyl, and —(C$_0$-C$_6$alkyl)-W—P(O)YR$^9$ZR$^{10}$.

17. The compound or salt of claim 1, wherein

R$^2$ is methyl or phenyl.

\* \* \* \* \*